United States Patent [19]

Albertson et al.

[11] 4,022,792
[45] May 10, 1977

[54] METHYLIDENEPIPERIDINES

[75] Inventors: Noel F. Albertson, Schodack;
William F. Michne, Clifton Park,
both of N.Y.

[73] Assignee: Sterling Drug Inc., New York, N.Y.

[22] Filed: May 27, 1976

[21] Appl. No.: 690,413

Related U.S. Application Data

[60] Division of Ser. No. 532,872, Dec. 16, 1974, Pat. No. 3,976,653, which is a division of Ser. No. 386,593, Aug. 8, 1973, Pat. No. 3,898,235, which is a continuation-in-part of Ser. No. 94,619, Dec. 2, 1970, Pat. No. 3,839,338, which is a continuation-in-part of Ser. No. 728,044, May 9, 1968, Pat. No. 3,639,411.

[52] U.S. Cl. .................... 260/293.83; 260/293.73; 260/293.76; 260/293.81
[51] Int. Cl.² ........................................ C07D 211/70

[58] Field of Search ................. 260/293.73, 293.76, 260/293.81, 293.83

[56] References Cited
UNITED STATES PATENTS 2,989,533   6/1961   Stein et al. ................. 260/294.3

*Primary Examiner*—G. Thomas Todd
*Attorney, Agent, or Firm*—B. Woodrow Wyatt; Theodore C. Miller

[57] ABSTRACT

1,2,3,4,4a,5,10,10a-Octahydro-5-($Y^3$)-5-($Y^4$)-benzo[g]quinolines and 1,2,3,4,4a,9b-hexahydro-5-($Y^3$)-5-($Y^4$)-5H-indeno[1,2,b]pyridines wherein $Y^3$ and $Y^4$ are hydrogen, alkyl or phenyl, which are useful as antagonists of strong analgesics, are obtained by cyclizing derivatives of 2-(phenyl or benzyl)-α-($Y^3$)-α-($Y^4$)-3-piperidinemethanols. The latter are obtained from corresponding 3-piperidinecarboxylic acids.

3 Claims, No Drawings

METHYLIDENEPIPERIDINES

CROSS REFERENCE TO RELATED APPLICATIONS

This application is a division of our copending application Ser. No. 532,872, filed Dec. 16, 1974, now U.S. Pat. No. 3,976,653, which is in turn a division of our copending application Ser. No. 386,593, filed Aug. 8, 1973, now U.S. Pat. No. 3,898,235, which is in turn a continuation-in-part of our copending application Ser. No. 94,619, filed Dec. 2, 1970, now U.S. Pat. No. 3,839,338, which is in turn a continuation-in-part of our copending application Ser. No. 728,044, filed May 9, 1968, now U.S. Pat. No. 3,639,411.

SUMMARY AND DETAILED DESCRIPTION OF THE INVENTION

This invention relates to compositions of matter classified in the art of chemistry as benzo[g]quinolines and indeno[1,2,b]pyridines, to processes for their preparation, and to intermediates for the same.

The invention sought to be patented resides in one composition aspect in the novel chemical compounds designated as 1,2,3,4,4a,5,10,10a-octahydro-1-($Y^1$)-7-($Y^2$)-5-($Y^3$)-5-($Y^4$)-benzo[g]quinolines and as 1,2,3,4,4a,9b-hexahydro-1($Y^1$)-7-($Y^2$)-5-($Y^3$)-5-($Y^4$)-5H-indeno[1,2,b]pyridines having in the free base form the formula

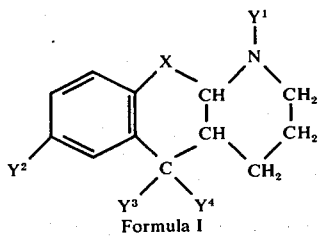

Formula I wherein:

X is —$CH_2$— or a valence bond;

$Y^1$ is alkyl containing 1–6 carbon atoms, 2,2-di(alkoxy)ethyl containing 4–6 carbon atoms, alkenyl containing 3–6 carbon atoms, alkynyl containing 3–6 carbon atoms, halo-alkenyl containing 3–6 carbon atoms and one or two chlorine or bromine atoms attached to ethylenic carbon, cyano-alkenyl containing 3–6 carbon atoms, cycloalkyl containing 3–7 carbon atoms, cycloalkenyl containing 5–6 carbon atoms, carbalkoxy containing 2–7 carbon atoms, di-alkylcarbamyl containing 3–5 carbon atoms, or (Z)-alkyl wherein alkyl contains 1–3 carbon atoms and Z is phenyl, cycloalkyl containing 3–7 carbon atoms, or cycloalkenyl containing 5–6 carbon atoms;

$Y^2$ is hydrogen, alkyl containing 1–4 carbon atoms, halo, trifluoromethyl, nitro, hydroxy, alkoxy containing 1–4 carbon atoms, trihalomethoxy, alkanoyloxy containing 1–12 carbon atoms, cycloalkanecarbonyloxy containing 4–8 carbon atoms, pyridinecarbonyloxy, alkanoylamino containing 1–12 carbon atoms, or alkanesulfonamido containing 1–12 carbon atoms;

$Y^3$ and $Y^4$ are the same or different and are hydrogen, alkyl containing 1–4 carbon atoms, or phenyl.

These compounds of Formula I are useful as antagonists of strong analgesics such as morphine and meperidine.

As will be appreciated, when X is the divalent methylene radical —$CH_2$—, Formula I defines the 1,2,3,4,4a,5,10,10a-octahydro-1-($Y^1$)-7-($Y^2$)-5-($Y^3$)-5-($Y^4$)-benzo[g]quinolines of this invention having in the free base form the formula

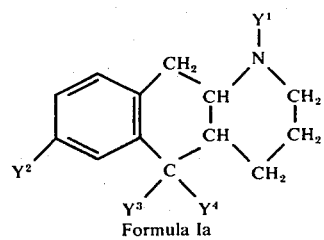

Formula Ia

And when X is a valence bond, Formula I defines the 1,2,3,4,4a,9b-hexahydro-1-($Y^1$)-7-($Y^2$)-5-($Y^3$)-5-($Y^4$)-5H-indeno[1,2,b]pyridines of this invention having in the free base form the formula

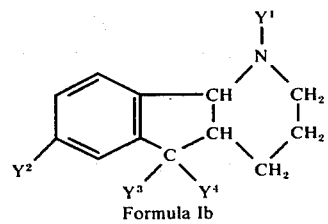

Formula Ib

When $Y^1$ is alkyl there are included for example methyl, ethyl, n-propyl, isopropyl, n-butyl, isoamyl, n-hexyl, and the like. When $Y^1$ is 2,2-di(alkoxy)ethyl there are included for example 2,2-dimethoxyethyl, 2,2-diethoxyethyl, and the like. When $Y^1$ is alkynyl there are included for example —C≡C—$CH_3$, —C≡C—$CH_2$—$CH_3$, —$CH_2$—C≡C—$CH_3$, —C≡C—CH($CH_3$)—$CH_3$, and the like. When $Y^1$ is alkenyl, there are included for example —CH=CH—$CH_3$, —C($CH_3$)=$CH_2$, —$CH_2$—CH=$CH_2$, —CH=C($CH_3$)$_2$, —CH=CH—$CH_2CH_2CH_3$, —$CH_2$—CH=CH—$CH_2CH_3$, and the like. When $Y^1$ is halo-alkenyl, there are included for example —CH=CH—Cl, —CH=CH—Br, —CCl=CHCl, —CCl—CHBr, —$CH_2$—CH=CCl—$CH_3$, —$CH_2$—CCl=CCl—$CH_3$, —CH=C(Cl)$_2$, —CBr=C($CH_3$)$_2$, —$CH_2$—CH=$CCl_2$, —$CH_2CH_2$—CH=CCl—$CH_3$, and the like. When $Y^1$ is cyano-alkenyl there are included for example —CH=CH—CN, —C(CN)=$CH_2$, —C($CH_3$)=CH—CN, —$CH_2$—CH=CH—CN, —$CH_2CH_2$—CH=CH—CN, —CH=CH—$CH_2CH_2CH_2$—CN, —CH=C(CN)$_2$, and the like. When $Y^1$ is cycloalkyl there are included for example cyclopropyl, 1-methylcyclopropyl, cyclobutyl, cyclopentyl, cyclohexyl, cycloheptyl, and the like. When $Y^1$ is cycloalkenyl there are included for example, cyclopenten-2-yl, cyclopenten-3-yl, 1-methylcyclopenten-1-yl, cyclohexen-2-yl, and the like. When $Y^1$ is di-alkylcarbamyl there are included dimethylcarbamyl and diethylcarbamyl. When $Y^1$ is (Z)-alkyl there are included for example benzyl, phenethyl, 2-phenylpropyl, cyclopropylmethyl, 1-cyclopropylmethyl, 2-cyclopropylethyl, cyclohexylmethyl, 3-cyclopentylpropyl, cyclopenten-1-ylmethyl, cyclopenten-2-ylmethyl, cyclohexen-2-ylmethyl, 3-(cyclohexen-3-yl)propyl, and the like.

When $Y^2$ is alkyl there are included for example methyl, ethyl, n-propyl, isopropyl, n-butyl, isobutyl, and the like. When $Y^2$ is halo there are included chlorine, bromine, fluorine and iodine. When $Y^2$ is alkoxy there are included for example methoxy, ethoxy, propoxy, isopropoxy, t-butoxy, and the like. When $Y^2$ is trihalomethoxy there are included trichloromethoxy and trifluoromethoxy. When $Y^2$ is alkanoyloxy there are included for example formoxy, acetoxy, propionoxy, isovaleroxy, dodecanoyloxy, and the like. When $Y^2$ is cycloakanecarbonyloxy there are included for example cyclopropanecarbonyloxy cyclobutanecarbonyloxy, cyclohexanecarbonyloxy, 1-methylcyclohexanecarbonyloxy, and the like. When $Y^2$ is pyridinecarbonyloxy there are included 2-pyridinecarbonyloxy, 3-pyridinecarbanyloxy, and 4-pyridinecarbonyloxy. When $Y^2$ is alkanoylamino there are included for example formamido, acetamido, propionamido, isovaleramido, heptanoylamino, dodecanoylamino, and the like. When $Y^2$ is alkanesulfonamido there are included for example methanesulfonamido, ethanesulfonamido, hexanesulfonamido, octanesulfonamido, undecanesulfonamido, and the like.

When $Y^3$ or $Y^4$ is alkyl there are included for example methyl, ethyl, n-propyl, isopropyl, isobutyl, and the like.

The invention sought to be patented resides in one process aspect in the process which comprises cyclizing a compound having in the free base form the formula

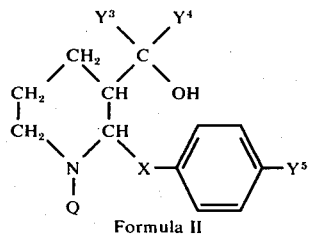
Formula II or a compound having in the free base form the formula

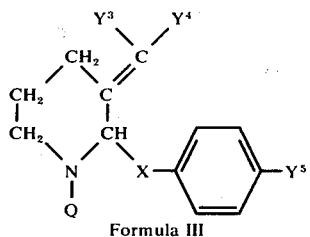
Formula III

Wherein $Y^3$ and $Y^4$ have the same significance indicated in Formula I above, $Y^5$ is hydrogen, alkyl containing 1–4 carbon atoms, halo, trifluoromethyl, or alkoxy containing 1–4 carbon atoms; and Q is hydrogen, alkyl containing 1–6 carbon atoms, aralkyl containing 7–10 carbon atoms, or acyl, by treatment with a strong organic or inorganic acid to yield a 1,2,3,4,4a,5,10,10a-octahydro-1-(Q)-7-($Y^5$)-5-($Y^3$)-5-($Y^4$)-benzo[g]quinoline or a 1,2,3,4,4a,9b-hexahydro-1-(Q)-7-($Y^5$)-5-($Y^3$)-5-($Y^4$-5H-indeno[1,2,b]pyridine having in the free base form the formula

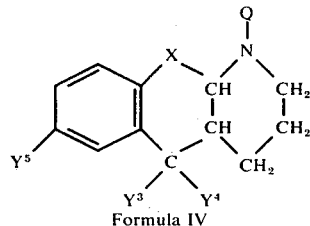
Formula IV wherein X, $Y^3$, $Y^4$, $Y^5$, and Q have the same significance indicated above.

The invention sought to be patented resides in a further process aspect in the process which comprises interacting a compound of Formula I except having H instead of $Y^1$ with an agent having the formula $Y^1$-An, wherein $Y^1$ has the same significance indicated in Formula I and An is the anion of a strong organic or inorganic acid, in the presence of an acid-absorbing medium, thereby forming a compound of Formula I.

The invention sought to be patented resides in a still further process aspect in the process which comprises interacting a compound of Formula IV except having H instead of Q with an acid halide or acid anhydride of an acid having the formula M—COOH and reducing the resulting amide, 1,2,3,4,4a,5,10,10a-octahydro-1-(M—CO—)-7-($Y^5$)-5-($Y^3$)-5-($Y^4$)-benzo[g]quinoline or 1,2,3,4,4a,9b-hexahydro-1-(M—CO—)-7-($Y^5$)-5-($Y^3$)-5-($Y^4$)-5H-indeno[1,2,b]pyridine, with lithium aluminum hydride to yield a 1,2,3,4,4a,5,10,10a-octahydro-1-(M—CH$_2$—)-7-($Y^5$-5-($Y^3$)-5-($Y^4$)-benzo[g]quinoline or 1,2,3,4,4a,9b-hexahydro-1-(M—CH$_2$—)-7-($Y^5$)-5-($Y^3$)-5-($Y^4$)-5H-indeno[1,2,b-]pyridine, wherein $Y^5$, $Y^3$, and $Y^4$ have the same significance indicated in Formula I and M is the residual moiety in those choices of Q which have the structural feature —CH$_2$— directly adjacent to, and attached to, the N atom in the 1-position of the benzo[g]quinolines or indeno[1,2,b]pyridines of Formula I.

The invention sought to be patented resides in a further composition aspect in the 1,2,3,4,4a,9b-hexahydro-1-(M—CO—)-5-($Y^3$)-5-($Y^4$)-7-($Y^2$)-5H-indeno[1,2,b]pyridines wherein: M is alkyl having 1–5 carbon atoms, or cycloalkyl having 3–7 carbon atoms, $Y^2$ is hydrogen, hydroxy, alkoxy having 1–4 carbon atoms, acetoxy, cycloalkanecarbonyloxy having 4–8 carbon atoms; and $Y^3$ and $Y^4$ are the same or different and are hydrogen, non-tertiary alkyl having 1–4 carbon atoms, or phenyl. These compounds are useful as intermediates as above-indicated. The related 1,2,3,4,4a,4,10,10a-octahydro-1-(M—CO—)-5-($Y^3$)-5-($Y^4$)-7-($Y^2$)-benzo[g]-quinolines are claimed in our above-identified co-pending application Ser. No. 94,619, filed Dec. 2, 1970.

The invention sought to be patented resides in a further composition aspect in the 1,2,3,4,4a,5,10,10a-octahydro-5-($Y^3$)-5-($Y^4$)-7-($Y^5$)-benzo[g]quinolines and 1,2,3,4,4a,9b-hexahydro-5-($Y^3$)-5-($Y^4$)-7-($Y^5$)-5H-indeno[1,2,b]pyridines wherein: $Y^3$ and $Y^4$ are the same or different and are hydrogen, alkyl having 1–4 carbon atoms or phenyl; and $Y^5$ is hydrogen, alkyl having 1–4 carbon atoms, halo, trifluoromethyl, or alkoxy having 1–4 carbon atoms. These compounds are useful as intermediates as above-indicated.

The invention sought to be patented resides in a further composition aspect in the 3-piperidinemethanols and the 3-methylidenepiperidines represented respectively in the free base form by Formulas II and III above which are useful intermediates in the preparation of the benzo[g]quinolines and indeno[1,2,b]pyridines of this invention.

The invention sought to be patented resides in the concept of several further composition and process aspects as set forth hereinbelow.

Certain 2-substituted piperidines, more particularly identified hereinafter, bearing in the 3-position one or two carboxy or carbo alkoxy groups, which are useful as intermediates in the preparation of the above 3-piperidinemethanol intermediates, are claimed in our above-identified U.S. Pat. No. 3,639,411, issued Feb. 1, 1972.

Due to the presence of the basic amino grouping, the free base forms represented by Formulas I, Ia, Ib, II, III, and IV above react with organic and inorganic acids to form acid-addition salts. The acid-addition salt forms are prepared from any organic or inorganic acid. They are obtained in conventional fashion, for instance either by direct mixing of the base with the acid or, when this is not appropriate, by dissolving either or both of the base and the acid separately in water or an organic solvent and mixing the two solutions, or by dissolving both the base and the acid together in a solvent. The resulting acid-addition salt is isolated by filtration, if it is insoluble in the reaction medium, or by evaporation of the reaction medium to leave the acid-addition salt as a residue. The acid moieties or anions in these salt forms are in themselves neither novel nor critical and therefore can be any acid anion or acid-like substance capable of salt formation with the base.

Representative acids for the formation of the acid-addition salts include formic acid, acetic acid, isobutyric acid, alpha-mercaptopropionic acid, trifluoroacetic acid, malic acid, fumaric acid, succinic acid, succinamic acid, tannic acid, glutamic acid, tartaric acid, oxalic acid, pyromucic acid, citric acid, lactic acid, glycolic acid, gluconic acid, saccharic acid, ascorbic acid, penicillin, benzoic acid, phthalic acid, salicyclic acid, 3,5-dinitrobenzoic acid, anthranilic acid, cholic acid, 2-pyridinecarboxylic acid, pamoic acid, 3-hydroxy-2-naphthoic acid, picric acid, quinic acid, tropic acid, 3-indoleacetic acid, barbituric acid, sulfamic acid, methanesulfonic acid, ethanesulfonic acid, isethionic acid, benzenesulfonic acid, p-toluenesulfonic acid, butylarsonic acid, methanephosphonic acid, acidic resins, hydrofluoric acid, hydrochloric acid, hydrobromic acid, hydriodic acid, perchloric acid, nitric acid, sulfuric acid, phosphoric acid, arsenic acid, and the like.

All of the acid-addition salts are useful as sources of the free base form, by reaction with an inorganic base. It will thus be appreciated that if one or more of the characteristics, such as solubility, molecular weight, physical appearance, toxicity, or the like of a given base or acid-addition salt thereof render that form unsuitable for the purpose at hand, it can be readily converted to another, more suitable form. For pharmaceutical purposes, acid-addition salts of relatively non-toxic, pharmaceutically-acceptable acids, for example hydrochloric acid, lactic acid, tartaric acid, and the like, are of course employed.

The compounds of Formula I, as well as certain of the intermediates as indicated hereinbelow, can exist in stereochemically isomeric forms, that is, optical isomers and geometric isomers. If desired, the isolation or the production of a particular stereochemical form can be accomplished by application of the general principles known in the prior art, and by the methods herein described.

The manner and process of making and using the invention, and the best mode contemplated by the inventors of carrying out this invention, will now be described so as to enable any person skilled in the art to which it pertains to make and use the same.

The process of this invention which comprises cyclizing a compound of Formula II or III by treatment with a strong organic or inorganic acid is conveniently and readily effected by relatively mild reaction temperatures, for instance, in the range 75°–100° C. The preferred acid for the cyclization is sulfuric acid, particularly in admixture with glacial acetic acid. However, other acids such as arylsulfuric acids or Lewis acids such as aluminum chloride are also satisfactory.

This cyclization process affords directly those species of Formula I, wherein $Y^1$ is hydrogen, lower alkyl, aralkyl, or acyl, and $Y^2$ is hydrogen, lower alkyl, halo, trifluoromethyl, or lower alkoxy. These species as well as those other species of Formula I wherein $Y^2$ is one of the other choices indicated in Formula I are obtained by interacting compounds of Formula I except having H in place of $Y^1$ with an alkylating agent having the formula $Y^1$-An, wherein $Y^1$ is as identified in Formula I An is the anion of a strong organic or inorganic acid, for instance a reactive halide or an arylsulfonate, e.g. a methylbenzenesulfonate, in the presence of an acid-absorbing medium, for instance an alkali metal carbonate or bicarbonate, e.g. sodium bicarbonate, thereby affording the desired 1,2,3,4,4a,5,10,10a-octahydro-1-($Y^1$)-7-($Y^2$)-5-($Y^3$)-5-($Y^4$)-benzo[g]quinolines and 1,2,3,4, 4a,9b-hexahydro-1-($Y^1$)-7-($Y^2$)-5-($Y^3$)-5-($Y^4$)-5H-indeno[1,2,b]-pyridines.

When $Y^1$ in these two groups of products has as a structural feature the divalent methylene radical, —$CH_2$—, at the point of attachment to the 1-position nitrogen atom, for instance hexyl, cyclopropylmethyl, and the like, a two-step indirect alkylation procedure can be employed. Thus, in the first step the starting material of Formula IV, wherein Q is hydrogen, is N-acylated by treatment with an appropriate acid halide or acid anhydride of an acid having the formula M-COOH, preferably in the presence of an acid-absorbing agent such as pyridine, thereby yielding an amide product, 1,2,3,4, 4a,5,10,10a-octahydro-1-(M-CO-)-7-($Y^5$)-5-($Y^3$)-5-($Y^4$)-benzo[g]quinoline or 1,2,3,4,4a,9b-hexahydro-1-(M-CO-)-7-($Y^5$)-5-($Y^3$)-5-($Y^4$)-5H-indeno[1,2,b]pyridine. In the second step, the amide product of the first step is reduced with lithium aluminum hydride to yield the desired 1,2,3,4,4a,5,10,-10a-octahydro-1-(M-$CH_2$—)-7-($Y^5$)-5-($Y^3$)-5-($Y^4$)-benzo[g]quinoline or 1,2,3,4,4a,9b-hexahydro-1-(M—$CH_2$—)-7-($Y^5$)-5-($Y^3$)-5-($Y^4$)-5H-indeno[1,2,b-]pyridine. As will be appreciated, in each instance M represents the residual moiety in those choices of $Y^1$ as defined in Formula I which have the formula M—$CH_2$—. Thus, for instance when $Y^1$ is hexyl, M is $CH_3$—($CH_2$)$_4$—, and of course M—COOH is $CH_3$-($CH_2$)$_4$—COOH, M—CO— is $CH_3$—($CH_2$)$_4$—CO—, and M—$CH_2$— is hexyl; and when $Y^1$ is cyclopropylmethyl, M is cyclopropyl, and of course M-COOH is cyclopropanecarboxylic acid, M—CO— is cyclopropanecarbonyl, and M-$CH_2$— is cyclopropylmethyl.

The species of Formula I where $Y^2$ is hydroxy are obtained by cleaving the corresponding alkoxy species with a suitable agent such as concentrated hydrobromic acid. By esterifying these hydroxy derivatives with a suitable O-alkanoylating or O-cycloalkanecarbonylating or O-pyridinecarbonylating agent there are obtained the species of Formula I wherein $Y^2$ is alkanoyloxy or cycloalkanecarbonyloxy or pyridinecarbonyloxy respectively.

The species of Formula I wherein $Y^2$ is nitro are obtained by nitrating the corresponding species wherein $Y^2$ is hydrogen. By reducing these nitro compounds to the corresponding amino compounds and N-acylating them with alkanoylating or alkanesulfonylating agents there are obtained the species of Formula I wherein $Y^2$ is alkanoylamino or alkanesulfonamido, respectively.

The species of Formula I wherein $Y^2$ is trihalomethoxy are prepared from the corresponding methoxy compounds by methods generally old in the art; for example see Senning, Chemical Reviews, 65, 393-394 (1965).

The intermediate 2-substituted-3-piperidinemethanols of Formula II are conveniently obtained from 1-(Q)-2-[p-($Y^5$)-phenyl-X-]-3,3-piperidinedicarboxylic acids, and lower alkyl esters thereof, wherein Q, $Y^5$, and X have the same significance indicated hereinabove, which form a further composition aspect of the instant invention. These acids and their lower alkyl esters are obtained by the following sequences of reactions of conventional type, both of which start with well-known and readily-available classes of compounds. Thus, when X is —$CH_2$—: A dialkyl 2-cyanoethylmalonate is acylated with a p-($Y^5$)-phenylacetyl chloride to yield a dialkyl [p-($Y^5$)-phenylacetyl](2-cyanoethyl)malonate. Catalytic hydrogenation of this product in the presence of platinum yields a dialkyl 2-[p-($Y^5$)-benzyl]-3,3-piperidinedicarboxylate which is then interacted with benzoyloxycarbonyl chloride to yield dialkyl 1-benzyloxycarbonyl-2-[p-($Y^5$)-benzyl]-3,3-piperidinedicarboxylate. By treatment with an equimolecular proportion of alcoholic strong alkali this diester is half-hydrolyzed to produce 1-benzyloxycarbonyl-2-[p-($Y^5$)-benzyl]-3-carbalkoxy-3-piperidinecarboxylic acid. When this acid is heated to decarboxylate it, there is obtained a mixture of the cis and trans isomers of a lower alkyl 1-benzyloxycarbonyl-2-[p-($Y^5$)-benzyl]-3-piperidinecarboxylate. (The cis and trans forms are readily separable by fractional crystallization and the subsequent steps in the reaction sequence either the pure isomers or mixtures thereof, as desired, can be employed.) When $Y_3$ and $Y_4$ are identical but are not hydrogen, these groups are introduced in a Grignard reaction by treating an alkyl 1-benzyloxycarbonyl-2-[p-($Y^5$)-benzyl]-3-piperidinecarboxylate with a Grignard reagent having the formula $Y^6$-Mg-halogen wherein $Y^6$ is one of the choices for $Y^3$ other than hydrogen, i.e. alkyl containing 1-4 carbon atoms or phenyl, thus yielding an alkyl 1-benzyloxycarbonyl-2-[p-($Y^5$)-benzyl]-$\alpha,\alpha$-di($Y^6$)-3-piperidinemethanol of Formula II wherein Q is benzyloxycarbonyl, X is —$CH_2$—, and $Y^3$ and $Y^4$ are each $Y^6$. This product can be used directly in the above-described cyclization process of this invention. Alternatively, the benzyloxycarbonyl group can be removed by catalytic hydrogenation in the presence of palladium catalyst to yield a lower alkyl 2-[p-($Y^5$)-benzyl]-$\alpha,\alpha$-di($Y^3$)-3-piperidinemethanol of Formula II wherein Q is hydrogen and X is —$CH_2$—. This product can be used as such in the cyclizaton process or can be N-acylated, N-alkylated, or N-aralkylated to introduce Q groups other than hydrogen before cyclization is effected.

When X in Formula II is a valence bond, the method of preparation of these intermediates is as follows: An alkyl [p-($Y^5$)-benzoyl]acetate is interacted with acrylonitrile in the presence of an alkali metal alkoxide to yield an alkyl $\alpha$-[p-($Y^5$)-benzoyl]-$\gamma$-cyanobutyrate, which is then catalytically hydrogenated in the presence of platinum to yield an alkyl 2-[p-($Y^5$)-phenyl]-3-piperidinecarboxylate. This product is interacted with benzyloxycarbonyl chloride to yield an alkyl 1-benzyloxycarbonyl-2-[p-($Y^5$)-phenyl]-3-piperidinecarboxylate. (In some instances, as specifically illustrated hereinbelow, the N-benzyloxycarbonylation step is not needed, and the Grignard reaction can be successfully applied directly.) The further steps using this product are the same as those described above for the corresponding 2-[p-($Y^5$)-benzyl] compounds.

The compounds of Formula II wherein $Y^3$ and $Y^4$ are each hydrogen are conveniently obtained by catalytically hydrogenating a lower alkyl 1-benzyloxycarbonyl-2-[p-($Y^5$)-phenyl-X]-3-piperidinecarboxylate in the presence of palladium catalyst to produce a lower alkyl 2-[p-($Y^5$)-phenyl-X]-3-piperidinecarboxylate which is reduced with lithium aluminum hydride, thus yielding the desired 2-[p-($Y^5$)-phenyl-X]-3-piperidinemethanol.

When $Y^3$ and $Y^4$ in the intermediate 2-substituted-3-piperidinemethanols of Formula II (and hence in the final products of Formula I) are unlike, the following modification of the preparative method is used. A 1-benzyloxycarbonyl-2-[p-($Y^5$)-phenyl-X]-3-piperidinecarboxylic acid is N-benzylated to yield a 1-benzyl-2-[p-($Y^5$)-phenyl-X-]-3-piperidinecarboxylic acid. This product is interacted with a $Y^6$ lithium to yield 1-benzyloxycarbonyl-2-[p-($Y^5$)-phenyl-X]-3-($Y^6$-CO-)-piperidine. This product can be reacted in a Grignard reaction with a $Y^6$-magnesium halide (wherein a different choice of $Y^6$ is of course made) to produce a 1-benzyloxycarbonyl-2-[p-($Y^5$)-phenyl-X-]-$\alpha$-$Y^6$-$\alpha$-$Y^6$-3-piperidinemethanol. The 1-benzyloxycarbonyl group is removed by catalytic hydrogenation, thus yielding a 2-[p-($Y^5$)-phenyl-X]-$\alpha$-($Y^6$)-$\alpha$-($Y^6$)-3-piperidinemethanol wherein the two $Y^6$ groups are different. Or, when it is desired that one of $Y^3$ and $Y^5$ in Formula II be hydrogen, the 1-benzyloxycarbonyl-2-[p-($Y^5$)-phenyl-X]-3-($Y^6$-CO-)-piperidine is reduced with lithium aluminum hydride to produce a 1-benzyloxycarbonyl-2-[p-($Y^5$)-phenyl-X]-$\alpha$-($Y^6$)-3-piperidinemethanol, from which the 1-benzyloxycarbonyl group is removed by catalytic hydrogenation. These products wherein $Y^3$ and $Y^4$ are unlike are of course then used in the same manner as described above for the corresponding products wherein the two $\alpha$-substituents are alike.

When the cis form of the 2-substituted-3-piperidinemethanol intermediates of Formula II are cyclized in accordance with this invention, the benzo[g]quinoline or indeno[1,2,b]pyridine products of Formula IV are almost wholly in the cis form. However, cyclization of the corresponding trans intermediates of Formula II yields the cis and the trans forms of the benzo[g]quinolines of indeno[1,2,b]pyridines in proportions which vary according to the identity of the Q substituent. For example, when trans-2-(p-methoxybenzyl)-$\alpha,\alpha$-dimethyl-3-piperidinemethanol was cyclized there was obtained the following proportions of cis and trans forms of the 1,2,3,4,4a,5,10,10a-octahydro-1-(Q)-7-methoxy-5,5-dimethylbenzo[g]quinoline:

| Q | % cis | % trans |
|---|---|---|
| H | — | 100 |
| $CH_3$ | 20 | 80 |
| $C_6H_4NO_2$-(p) | 35 | 65 |
| $CH_3CO$ | 60 | 40 |
| $SO_2C_6H_4NO_2$-(p) | 80 | 20 |

Thus by appropriate choice of the Q substituent, the proportion of the cis and trans cyclization products can be adjusted as desired.

Although the 2-substituted-3-piperidinemethanols of Formula II are ordinarily the preferred intermediates, there can also be used the corresponding olefin forms represented by Formula III, which appear in at least some instances to be formed during the cyclization of the compounds of Formula II. The 1-(Q)-2-[p-($Y^5$)-phenyl-X-]-3-[($Y^3$)($Y^4$)methylidene]piperidines of Formula III wherein Q is benzyloxycarbonyl, are isolable as by-products from the hydrogenolysis of the 1-benzyloxycarbonyl-2-[p-($Y^5$)-phenyl-X-]-$\alpha$-($Y^3$)-$\alpha$-($Y^4$)-3-piperidinemethanols and can be cyclized as such or after removal of the benzyloxycarbonyl group by hydrogenolysis followed, if desired, by N-alkylation, N-aralkylation, or N-acylation to introduce other Q groups.

The structures of the compounds of this invention were established by the modes of synthesis, by elementary analysis, and by ultraviolet, infrared, and nuclear magnetic resonance spectra. The course of the reactions and homogeneity of the products were ascertained by thin layer chromatography.

The invention is illustrated by the following examples without, however, being limited thereto. The melting points were determined by the capillary method and are uncorrected.

EXAMPLE 1

A. A mixture of 53.3 g. of diethyl (2-cyanoethyl)-malonate, 6.0 g. of sodium hydride, and 275 ml. of toluene was refluxed for five hours, 250 ml. of toluene was then added and refluxing was continued for a further period of 2 hours. The mixture was then cooled below 5° C. in an ice bath and there was added dropwise a solution of 50.7 g. of p-methoxyphenylacetyl chloride in 100 ml. of toluene. After addition of the acid chloride was completed, the temperature of the reaction mixture was allowed to rise to room temperature. The mixture was then stirred for one hour, diatomaceous silica filter aid (Filter—Cel—Johns-Manville) was added, and the mixture was filtered. The filtrate was concentrated under reduced pressure to yield 80.3 g. of a clear yellow oil. This oil was fractionally distilled under reduced pressure. The fraction distilling at 169°–174° C. at 0.4 mm. pressure weighed 12.6 g. and had $n_D^{25} = 1.4989$. This product was diethyl (p-methoxyphenylacetyl)(2-cyanoethyl)malonate.

B. 10.8 g. of diethyl (p-methoxyphenylacetyl)(2-cyanoethyl)malonate was diluted with glacial acetic acid to a volume of 100 ml., 0.5 g. of platinum oxide was added, and catalytic hydrogenation at 50 pounds hydrogen pressure was carried out for 2½ hours, the theoretical amount of hydrogen being absorbed during this period. The hydrogenation mixture was filtered and the filtrate was concentrated under reduced pressure. The resulting residue, which contained some crystals, was partitioned between dilute hydrochloric acid and diethyl ether. The layers were separated, and after adding ice to the aqueous layer it was made basic by addition of ammonium hydroxide and extracted twice with diethyl ether. The ethereal extracts were combined, washed with water, and dried over anhydrous calcium sulfate, and ethereal hydrogen chloride was added dropwise while cooling the mixture in an ice bath. A somewhat gummy crystalline solid separated from solution. After adding a few milliliters of ethyl alcohol to dissolve away the gummy material the solid was collected on a filter, was washed with diethyl ether, and was dried at 70° C. The resulting product, which weighed 6.4 g., was recrystallized twice from ethanol-diethyl ether to yield 4.9 g. of diethyl 2-(p-methoxybenzyl)-3,3-piperidinedicarboxylate hydrochloride as a white crystalline solid which melted at 163°–165° C.

C. To a mixture of 252 g. of diethyl 2-(p-methoxybenzyl)-3,3-piperidinedicarboxylate hydrochloride, 123 g. of benzyloxycarbonyl chloride, and 1200 ml. of chloroform there was added dropwise 145 g. of triethylamine while maintaining the temperature of the reaction mixture at approximately 25° C. by occasional cooling. After the addition of triethylamine was complete, the reaction mixture was stirred for one hour, then was washed successively with water, dilute hydrochloric acid, and a saturated aqueous solution of sodium bicarbonate and dried over anhydrous calcium sulfate. The reaction mixture was filtered, and the filtrate was concentrated to yield 333 g. of diethyl 1-benzyloxycarbonyl-2-(p-methoxybenzyl)-3,3-piperidinedicarboxylate as a clear yellow oil.

D. A mixture of 257 g. of diethyl 1-benzyloxycarbonyl-2-(p-methoxybenzyl)-3,3-piperidinedicarboxylate, 35 g. of 86 percent potassium hydroxide, 530 ml. of ethyl alcohol, and 530 ml. of water was stirred and refluxed for seven and one-half hours. The reaction mixture was concentrated under reduced pressure until only water distilled. More water was added to the reaction mixture, which was then extracted twice with diethyl ether. The ether extracts were combined, washed with water, dried, filtered, and the filtrate was concentrated under reduced pressure to recover 108 g. of unhydrolyzed diester starting material. The aqueous layers from the extractions were combined and acidified with concentrated hydrochloric acid, causing separation of an oil. This oil crystallized when shaken with a few ml. of diethyl ether. The mixture was filtered and the solid thus collected was washed with diethyl ether and air-dried. This product was a first crop of 1-benzyloxycarbonyl-2-(p-methoxybenzyl)-3-carbethoxy-3-piperidinecarboxylic acid. By repeating the hydrolysis procedure on the 108 g. of recovered diethyl 1-benzyloxycarbonyl-2-(p-methoxybenzyl)-3,3-piperidinedicarboxylate, using 14.6 g. of 86 percent potassium hydroxide, 225 ml. of ethyl alcohol, and 225 ml. of water, there was obtained a second crop of 1-benzyloxycarbonyl-2-(p-methoxybenzyl)-3-carbethoxy-3-piperidinecarboxylic acid. The two crops were combined and recrystallized from ethyl alcohol to yield 157 g. of this product as a white solid. When crystallized from ethyl alcohol, this compound melted at 186°–188° C. (dec.); ir (K.Br) 1740 (ester C=O), 1720 (acid C=O), and 1650 cm$^{-1}$ (urethane C=O).

E. 157 g. of 1-benzyloxycarbonyl-2-(p-methoxybenzyl)-carbethoxy-3-piperidinecarboxylic acid was heated in an ethylene glycol bath at 190°–200° C. until gas evolution had ceased. The resulting product was cooled and dissolved in diethyl ether, and the ether solution was washed with saturated aqueous sodium bicarbonate solution, dried, and filtered. The filtrate was concentrated by evaporation to yield 131 g. of clear, yellow syrup. This syrup was dissolved in 328 ml. of ethyl alcohol and the solution was cooled in a refrigerator overnight. The white crystalline solid which separated from solution was collected on a filter, washed with ethyl alcohol, and dried at 50° C. under reduced pressure. This product which weighed 80 g. and melted at 68°–71° C. was cis ethyl 1-benzyloxycarbonyl-2-(p-methoxybenzyl)-3-piperidinecarboxylate. (The corresponding acid, cis-1-benzyloxycarbonyl-2-(p-methoxybenzyl)-3-piperidinecarboxylic acid, was a white crystalline solid which melted at 174°–175° C.)

The mother liquor from the above crystallization was concentrated under reduced pressure to yield 49 g. of a clear syrup consisting of a trans-rich mixture of the cis and trans forms of ethyl 1-benzyloxycarbonyl-2-(p-methoxybenzyl)-3piperidinecarboxylate.

By adding 1.0 ml. of concentrated hydrochloric acid to 6.05 g. of cis ethyl 1-benzyloxycarbonyl-2-(p-methoxybenzyl)-3-piperidinecarboxylate to convert the latter to its hydrochloride, diluting to a total volume of 60 ml. with water, and catalytically hydrogenating in the presence of palladium-on-charcoal catalyst there was obtained 3.0 g. of cis ethyl 2-(p-methoxybenzyl)-3-piperidinecarboxylate hydrochloride as a white crystalline solid which melted at 139°–142° C. Similarly, 20.6 g. of a trans-rich mixture of the cis and trans forms of ethyl 1-benzyloxycarbonyl-2-(p-methoxybenzyl)-3-piperidinecarboxylate hydrochloride was catalytically hydrogenated in the presence of palladium-on-charcoal catalyst to produce a transrich mixture of the cis and trans forms of ethyl 2-(p-methoxybenzyl)-3-piperidinecarboxylate hydrochloride. This salt was converted to 10.4 g. of the free base by treatment with ammonium hydroxide; and then the free base was converted in ethyl acetate solution to the p-toluenesulfonate salt, which was isolated and recrystallized from anhydrous ethanol-diethyl ether to yield 6.8 g. of trans ethyl 2-(p-methoxybenzyl)-3-piperidinecarboxylate p-toluenesulfonate as a white crystalline solid which melted at 140°–142° C.

Reduction of 8.2 g. of cis ethyl 1-benzyloxycarbonyl-2-(p-methoxybenzyl)-3-piperidinecarboxylate with 1.52 g. of lithium aluminum hydride in 97 ml. of tetrahydrofuran yielded cis-1-methyl-2-(p-methoxybenzyl)-3-piperidinemethanol, isolated as its hydrochloride (in a yield of 2.8 g.), a white crystalline solid which melted at 185°–186° C. trans-1-Methyl-2-(p-methoxybenzyl)-3-piperidinemethanol, a white crystalline solid which melted at 66°–68° C., can be obtained in similar fashion.

F. To a mixture of 7.2 g. of magnesium turnings and 75 ml. of anhydrous diethyl ether there was gradually added a solution of 42.6 g. of methyl iodide in 75 ml. of anhydrous diethyl ether at a rate sufficient to maintain the reaction mixture at gentle reflux. When this addition was completed, the reaction mixture was stirred and refluxed for one hour, and then there was added in a fine stream a solution of 24.5 g. of cis ethyl 1-benzyloxycarbonyl-2-(p-methoxybenzyl)-3-piperidinecarboxylate in 375 ml. of anhydrous diethyl ether. The resulting reaction mixture was stirred and refluxed for three hours and then was poured into water containing 25 ml. of concentrated hydrochloric acid. More diethyl ether was added, the mixture was shaken, and the ethereal layer was separated, washed with saturated aqueous sodium bicarbonate solution, dried, and filtered. The filtrate was concentrated under reduced pressure to yield 21.5 g. of cis-1-benzyloxycarbonyl-2-(p-methoxybenzyl)-$\alpha,\alpha$-dimethyl-3-piperidinemethanol as a syrup; ir ($CHCl_3$) 3600 (free OH), 3450 (bonded OH), 1680 (C = O), 1250 and 1040 (ether), and 820 and 690 cm$^{-1}$ (1,4-di- and monosubstituted benzene).

Proceeding in the manner described above but using in place of the cis form, 49 g. of the trans-rich mixture of cis and trans ethyl 1-benzyloxycarbonyl-2-(p-methoxybenzyl)-3-piperidinecarboxylate obtained as described in the latter portion of part E, and using a Grignard reagent prepared by mixing 14.4 g. of magnesium turnings and 150 ml. of diethyl ether with 85.1 g. of methyl iodide in 150 ml. of diethyl ether, there was obtained as the product 42.8 g. of a trans-rich mixture of cis- and trans-1-benzyloxycarbonyl-2-(p-methoxybenzyl)-$\alpha,\alpha$-dimethyl-3-piperidinemethanol as a syrup. The infrared spectrum of this product was almost identical with that of the cis product, minor differences being observed in the 1,600–1,000 cm.$^{-1}$ region.

G. 21.5 g. of cis-1-benzyloxycarbonyl-2-(p-methoxybenzyl)-$\alpha,\alpha$-dimethyl-3-piperidinemethanol was mixed with 4.5 ml. of concentrated hydrochloric acid and diluted with 95 percent ethyl alcohol to a volume of 200 ml. This solution was subjected to catalytic hydrogenation in the presence of 10 percent palladium-on-charcoal catalyst for approximately two hours. The reaction mixture was filtered to remove the catalyst, and the filtrate was concentrated by evaporation under reduced pressure. The residue thus obtained was partitioned between water and diethyl ether. The aqueous layer was made basic with ammonium hydroxide and extracted with diethyl ether. The ether extract was washed with water and dried over anhydrous calcium sulfate. The ether extract was filtered and the filtrate was concentrated to yield 10.4 g. of cis-2-(p-methoxybenzyl)-$\alpha,\alpha$-dimethyl-3-piperidinemethanol as a syrup. A solution of this base in 90 ml. of ether acetate was mixed with 6.6 g. of p-toluenesulfonic acid hydrate in 60 ml. of ethyl acetate. The solid which formed was collected on a filter, washed with ethyl acetate, and dried at 50° C. overnight under reduced pressure. The product was then recrystallized from ethyl alcohol to yield 11.8 g. of cis-2-(p-methoxybenzyl)-$\alpha,\alpha$-dimethyl-3-piperidinemethanol p-toluenesulfonate. This salt was a white solid which melted at 204°–206° C. When 3.04 g. of this salt was treated with 0.5 ml. of acetyl chloride in the presence of 2.0 ml. of triethylamine in 60 ml. of chloroform there was obtained 1.1 g. of cis-1-acetyl-2-(p-methoxybenzyl)-$\alpha,\alpha$-dimethyl-3-piperidinemethanol as a white crystalline solid which melted at 138°–140° C.

190 g. of trans-rich mixture of cis- and trans-1-benzyloxycarbonyl-2-(p-methoxybenzyl)-$\alpha,\alpha$-dimethyl-3-piperidinemethanol obtained in the manner described above in the latter portion of part F was mixed with 40 ml. of concentrated hydrochloric acid and 5 g. of 10% palladium-on-charcoal catalyst, and the resulting mixture was diluted to a volume of 1,800 ml. with 95 percent ethyl alcohol. This mixture was hydrogenated under a hydrogen pressure of 435 pounds per square inch for seven hours, hydrogen consumption ceasing after four hours. The reaction mixture was filtered through Filter-Cel using a small quantity of 95 percent ethyl alcohol as a rinse. The combined filtrate and rinse was evaporated to dryness under reduced pressure. The residue was partitioned between water and diethyl ether, and the aqueous layer was made basic with concentrated ammonium hydroxide and extracted with ether. The ether extract was washed with water, dried, filtered, and evaporated to dryness under reduced pressure to give 93 g. of syrupy product. This material was taken up in 500 ml. of diethyl ether and slowly treated with 170 ml. (one equivalent) of 2N ethanolic hydrogen chloride. The resulting solution was cooled for several hours at 0° C. to give, after filtration and washing with ether, 43 g. of trans-2-(p-methoxybenzyl)-α,α-dimethyl-3-piperidinemethanol hydrochloride which melted at 156°–159° C. After recrystallization, this product melted at 158°–159° C., $R_f$ .42 (silica, CHCl$_3$, 3% isopropyl amine), mixture with cis isomer showed two spots, $R_f$ .38 and .42; ir (KBr) 1250 and 1030 (ether) and 820 cm.$^{-1}$ (1,4-disubstituted benzene). When 1.8 g. of this salt was treated with 0.43 ml. of acetyl chloride in the presence of 1.68 ml. of triethylamine in 18 ml. of chloroform there was obtained 1.4 g. of trans-1-acetyl-2-(p-methoxybenzyl)-α,α-dimethyl-3-piperidinemethanol as a white crystalline solid which melted at 111°–113° C.

Interaction of 3.04 g. of cis-2-(p-methoxybenzyl)-α,α-dimethyl-3-piperidinemethanol p-toluenesulfonate with 1.55 g. of p-nitrobenzenesulfonyl chloride at room temperature in a mixture of 2.0 ml. of triethylamine and 60 ml. of chloroform yielded 2.2 g. of cis-1-(p-nitrobenzenesulfonyl)-2-(p-methoxybenzyl)-α,α-dimethyl-3-piperidinemethanol as a yellow solid which melted at 182°–184° C. In similar fashion, interaction of 2.20 g. of trans-2-(p-methoxybenzyl)-α,α-dimethyl-3-piperidinemethanol hydrochloride with 1.62 g. of p-nitrobenzenesulfonyl chloride at room temperature in a mixture of 2.1 ml. of triethylamine and 40 ml. of chloroform yielded 2.55 g. of trans-1-(p-nitrobenzenesulfonyl)-2-(p-methoxybenzyl)-α,α-dimethyl-3-piperidinemethanol as a yellow solid which melted at 132°–134° C.

A mixture of 2.2 g. of trans-2-(p-methoxybenzyl)-α,α-dimethyl-3-piperidinemethanol hydrochloride, 0.65 ml. of 35% aqueous formaldehyde solution, and 1.1 ml. of triethylamine was diluted to a total volume of 50 ml. with ethanol and catalytically hydrogenated in the presence of palladium-on-charcoal catalyst. From the resulting reaction mixture there was obtained 1.0 g. of trans-1,α,α-trimethyl-2-(p-methoxybenzyl)-3-piperidinemethanol as a white crystalline solid which melted at 78°–79° C. In similar fashion, catalytic hydrogenation of a mixture of 2.6 g. of cis-2-(p-methoxybenzyl)-α,α-dimethyl-3-piperidinemethanol and 0.75 ml. of 35% aqueous formaldehyde solution in ethanol yielded 1.4 g. of cis-1,α,α-trimethyl-2-(p-methoxybenzyl)-3-piperidinemethanol as an off-white crystalline solid which melted at 94°–96° C.

H. A mixture of 8.0 g. of cis-2-(p-methoxybenzyl)-α,α-dimethyl-3-piperidinemethanol p-toluenesulfonate, 65 ml. of glacial acetic acid, and 13 ml. of concentrated sulfuric acid was heated on a steam bath for 10 minutes, poured into water, made basic with concentrated ammonium hydroxide, and extracted with ether. The extract was washed with water, dried, filtered, and evaporated to dryness under reduced pressure to give 3.6 g. of crude product. A thin layer chromatogram (alumina, 95% chloroform/5% methanol) showed the major product at $R_f$ = .18 and a faint trace at $R_f$ = .50. The residue was taken up in ether and treated with a slight excess of ethanolic hydrogen chloride. The hydrochloride which precipitated was recrystallized from 95 percent ethyl alcohol. This product, which was cis-1,2,3,4,4a,5,10,10a-octahydro-7-methoxy-5,5-dimethylbenzo[g]quinoline hydrochloride melted at 225° C.; ir (KBr) 1250 and 1050 (ether) and 870 and 800 cm.$^{-1}$ (1,2,4-substituted benzene); nmr (of base, CDCl$_3$) 420–390 (m,3), 223 (s,3) 78,73 (singlets, 6 total), 220–50 (broad envelope, 11).

A mixture of 4.5 g. of trans-2-(p-methoxybenzyl)-α,α-dimethyl-3-piperidinemethanol hydrochloride, 25 ml. of glacial acetic acid, and 5 ml. of concentrated sulfuric acid was heated on a steam bath for twelve minutes, poured into water, made basic with concentrated ammonium hydroxide, and extracted with ether. The extract was washed with water, dried, filtered, and evaporated to dryness under reduced pressure to give 3.2 g. of product. A thin layer chromatogram (alumina, chloroform / 5% methanol) showed a faint trace at $R_f$ = .18 with the major component at $R_f$ = .50. The residue was taken up in diethyl ether and treated with a slight excess of ethanolic hydrogen chloride. The hydrochloride which precipitated was recrystallized from 95 percent ethyl alcohol. This product, which was trans-1,2,3,4,4a,5,10,10a-octahydro-7-methoxy-5,5-dimethylbenzo[g]quinoline hydrochloride, melted at 295°–298° C.; ir (KBr) 1240 and 1040 (ether) and 860 and 830 cm.$^{-1}$ (1,2,4-trisubstituted benzene); nmr (of base, CDCl$_3$) 420–390 (m,3), 224 (s,3), 78 and 67 (singlets, 3 each) 200–50 (broad envelope, 11).

Interaction of 2.20 g. of cis-1,2,3,4,4a,5,10,10a-octahydro-7-methoxy-5,5-dimethylbenzo[g]quinoline hydrochloride with 1.73 g. of p-nitrobenzenesulfonyl chloride at room temperature in a mixture of 2.2 ml. of triethylamine and 40 ml. of chloroform yielded 2.77 g. of cis-1,2,3,4,4a,5,10,10a-octahydro-1-(p-nitrobenzenesulfonyl)-7-methoxy-5,5-dimethylbenzo[g]quinoline as a yellow solid which melted at 176°–178° C. Similarly, using the trans form of the starting material in this acylation, there was obtained 2.03 g. of trans-1,2,3,4,4a,5,10,10a-octahydro-1-(p-nitrobenzenesulfonyl)-7-methoxy-5,5-dimethylbenzo[g]quinoline as an off-white solid which melted at 203°–205° C.

EXAMPLE 2

A. cis-1,2,3,4,4a,5,10,10a-Octahydro-7-methoxy-5,5-dimethylbenzo[g]quinoline hydrochloride was treated with dilute ammonium hydroxide, and the free base thus obtained was dried in ether. After filtration and evaporation of the solvent under reduced pressure, the residue which weighed 0.7 g. was mixed with 2 ml. of formic acid and 2 ml. of 35% aqueous formaldehyde solution and the mixture was heated on a steam bath for 1½ hours. The reaction mixture was diluted with water, made basic with concentrated ammonium hydroxide and extracted with diethyl ether. The ether extract was washed with water, dried, filtered, and evaporated to dryness under reduced pressure. The residue (0.7 g.) was distilled, b.p. (0.03 mm.) 105°–110° C; ir (thin film) 1240 and 1050 (ether) and 870 and 800 (1,2,4-trisubstituted benzene); nmr (CDCl$_3$) 224 (s,3), 145 (s,3), 79 and 74 (singlets, 3 each). This product was cis-1,2,3,4,4a,5,10,10a-octahydro-7-methoxy-1,5,5-trimethylbenzo[g]quinoline.

A mixture of 2.0 g. of this base, 1.2 g. of methyl iodide, and 20 ml. of acetonitrile was allowed to stand at room temperature. Crystallization occurred within 1 hour. After cooling the mixture in ice for several hours, there was obtained 2.7 g. of cis-1,2,3,4,4a,5,10,10a-octahydro-7-methoxy-1,5,5-trimethylbenzo[g]quinoline methiodide, m.p. 286° C. (dec.). Recrystallization from water brought the melting point of this product to 288°–293° C. (dec.).

B. Using the same manipulative procedure as that described in part A, 5.6 g. of trans-1,2,3,4,4a,5,10,10a-octahydro-7-methoxy-5,5-dimethylbenzo[g]quinoline hydrochloride was treated with dilute ammonium hydroxide to yield 4.9 g. of the corresponding free base which was treated with formic acid and 35% aqueous formaldehyde solution to yield 5.0 g. of crude product which was distilled. There was thus obtained trans-1,2,3,4,4a,5,10,10a-octahydro-7-methoxy-1,5,5-trimethylbenzo[g]quinoline as a clear liquid, b.p. (0.02 mm.) 120° C.; ir (film) 850 and 790 cm.$^{-1}$ (1,2,4-trisubstituted benzene); nmr (CDCl$_3$) 221 (s,3),138 (s,3), 78 and 65 (singlets, 3 each). A 0.7 g. portion of this base was interacted with 0.7 g. of methyl iodide in acetonitrile to yield 0.95 g. of the methiodide, m.p. 301°–305° C. (dec.).

EXAMPLE 3

A mixture of 3.0 g. of cis-1,2,3,4,4a,5,10,10a-octahydro-7-methoxy-5,5-dimethylbenzo[g]quinoline hydrochloride, 1.8 g. of n-propyl iodided, 2.5 g. of sodium bicarbonate, and 40 ml. of dimethylformamide was stirred and refluxed for three hours. The reaction mixture was concentrated under reduced pressure and the resulting residue was partitioned between water and diethyl ether. The ether layer was washed with water, dried, treated with decolorizing charcoal, and filtered, and the filtrate was concentrated to yield 2.5 g. of a syrup. This product, a base, was treated with ethanolic hydrogen chloride and the resulting base hydrochloride was recrystallized and converted back to the free base by treatment with aqueous sodium hydroxide solution to yield 1.3 g. of cis-1,2,3,4,4a,5,10,10a-octahydro-1-propyl-7methoxy-5,5-dimethylbenzo[g]quinoline as a syrup. This base was dissolved in a mixture of chloroform and methanol and chromatographed on 130 g. of alumina, eluting with chloroform. The base thus obtained was converted to the hydrochloride (0.8 g.) by treatment with ethanolic hydrogen chloride. Recrystallization of this product from ethanol-diethyl ether yielded 0.7 g. of cis-1,2,3,4,4a,5,10,10a-octahydro-1-propyl-7-methoxy-5,5-dimethylbenzo[g]quinoline hydrochloride as a white crystalline solid which melted at 201–202°.

EXAMPLE 4

A mixture of 0.56 g. of cis-1,2,3,4,4a,5,10,10a-octahydro-7-methoxy-5,5-dimethylbenzo[g]quinoline hydrochloride, 0.27 g. of sodium acetate trihydrate, and 7 ml. of acetic anhydride was stirred and heated on a steam bath for three hours. The reaction mixture was evaporated to dryness under reduced pressure, and the resulting residue was partitioned between water and diethyl ether. The ether layer was washed with 1N-hydrochloric acid and with saturated aqueous sodium bicarbonate solution. After drying the ethereal solution, filtering, and removing the solvent by evaporation under reduced pressure, there was obtained 0.52 g. of a syrup which crystallized from hexane to yield cis-1-acetyl-1,2,3,4,4a,5,10,10a-octahydro-7-methoxy-5,5-dimethylbenzo[g]quinoline, m.p. 81°–85° C.; ir (CHCl$_3$), 1630 cm.$^{-1}$ (C=O); nmr (CDCl$_3$), 80 (s,3), 78 (s,3).

In similar fashion 1.06 g. of trans-1,2,3,4,4a,5,10,-10a-octahydro-7-methoxy-5,5-dimethyl-benzo[g]quinoline hydrochloride was N-acetylated to yield 1.0 g. of trans-1-acetyl-1,2,3,4,4a,5,10,10a-octahydro-7-methoxy-5,5-dimethyl-benzo[g]-quinoline m.p. 157°–159° C.; ir (CHCl$_3$), 1630 cm.$^{-1}$ (C=O); nmr (CHCl$_3$) 80 (s,3), 68 (s,3).

EXAMPLE 5

A mixture of 2.2 g. of cis-1,2,3,4,4a,5,10,10a-octahydro-7-methoxy-5,5-dimethyl-benzo[g]quinoline hydrochloride, 1.73 g. of p-nitrobenzenesulfonyl chloride, 40 ml. of chloroform and 2.2 ml. of triethylamine was allowed to stand for twenty-four hours at room temperature. The reaction mixture was then washed successively with a 40 ml. portion each of water, 1N-hydrochloric acid, and saturated aqueous sodium bicarbonate solution. After drying, filtration, and evaporation of the solvent under reduced pressure, there was obtained 3.4 g. of crude product. This was dissolved in 10 ml. of warm chloroform, diluted with 60 ml. of hot ethanol, and cooled. The product was filtered, washed with ethanol, and dried at 50° C. under reduced pressure to give 2.8 g. of cis-1-(p-nitrobenzenesulfonyl)-1,2,3,4,4a,5,10,10a-octahydro-7-methoxy-5,5-dimethylbenzo[g]quinoline, m.p. 176°–178° C.; ir (KBr) 1530 and 1350 cm.$^{-1}$ (NO$_2$), 1350 and 1160 (SO$_2$); nmr (CDCl$_3$) 489 (A$_2$B$_2$,4), 223 (s,3), 75 and 77 (singlets, 6).

In similar fashion, 3.0 g. of trans-1,2,3,4,4a,5,10,10a-octahydro-7-methoxy-5,5-dimethylbenzo[g]quinoline hydrochloride was converted to trans-1-(p-nitrobenzenesulfonyl)-1,2,3,4,4a,5,10,10a-octahydro-7-methoxy-5,5-dimethylbenzo[g]quinoline, m.p. 203°–205° C.; ir (KBr) 1530 and 1350 (NO$_2$) and 1350 and 1160 (SO$_2$); nrm (CDCl$_3$) 487 (A$_2$B$_2$,4), 224 (s,3), 76 and 60 (singlets, 3 each).

EXAMPLE 6

Interaction of 15.1 g. of crude 2-(p-methoxybenzyl)-α,α-dimethyl-3-piperidinemethanol with 10.9 g. of p-toluenesulfonyl chloride in 150 ml. of pyridine yielded 15.9 g. of 1-(p-toluenesulfonyl)-2-(p-methoxybenzyl)-α,α-dimethyl-3-piperidinemethanol as a red syrup. Proceeding in a manner similar to that described above in part H of Example 1, 14.5 g. of this red syrup was heated with a mixture of 75 ml. of glacial acetic acid and 15 ml. of concentrated sulfuric acid to yield 3.3 g. of crude 1,2,3,4,4a,5,10,10a-octahydro-1-(p-toluenesulfonyl)-7-methoxy-5,5-dimethylbenzo[g]quinoline as a light brown solid which melted at 112°–115° C. By chromatographing this product on alumina, using a hexane and chloroform mixture in volume/volume ratio of 75/25, there was obtained 1.9 g. of cis-1,2,3,4,4a,5,10,10a-octahydro-1-(p-toluenesulfonyl)-7-methoxy-5,5,-dimethylbenzo[g]quinoline as a white crystalline solid which melted at 130°–133° C. The corresponding trans compounds, obtained in a yield of 2.7 g. by interacting 4.2 g. of trans-1,2,3,4,4a,5,10,10a-octahydro-7-methoxy-5,5-dimethylbenzo[g]quinoline with 2.9 g. of p-toluenesulfonyl chloride in the presence of 50 ml. of pyridine, was a white crystalline solid which melted at 165°–167° C.

EXAMPLE 7

A solution of 71.4 g. of a crude mixture of cis- and trans-1,2,3,4,41,5,10,10a-octahydro-7-methoxy-5,5-dimethylbenzo[g]quinoline (determined by nuclear magnetic resonance spectral measurement to contain approximately 60% of the cis isomer) in 700 ml. of 48% hydrobromic acid was refluxed for one and one-half hours and allowed to cool slowly. This caused crystallization of 47.4 g. of cis-1,2,3,4,4a,5,10,10a-octahydro-5,5-dimethylbenzo[g]quinolin-7-ol hydrobromide. This was recrystallized from methanol-ether to give 41.5 g. of this product which melted at 333°–336° C.

Slow evaporation of the mother liquor from the first crystallization under reduced pressure caused crystallization of 14.1 g. of trans-1,2,3,4,4a,5,10,10a-octahydro-5,5-dimethylbenzo[g]quinoline7-ol hydrobromide. This product melted at 294°–298° C. after recrystallization from methanol-ether.

The cis base was obtained by stirring a suspension of 41.5 g. of the cis hydrobromide in 400 ml. of water and 100 ml. of concentrated ammonium hydroxide on a steam bath for one-half hour, cooling, and filtering. After washing with water and drying to constant weight, there was obtained 29.4 g. of cis-1,2,3,4,4a,5,10,10a-octahydro-5,5-dimethylbenzo[g]quinolin-7-ol. After a recrystallization from ethanol, this base melted at 214°–216° C.; (nmr DMSO-$d_6$) methyl singlets at 72 and 68 Hz.

The trans base was similarly obtained from the trans hydrobromide in 92% yield; nmr (DMSO-$d_6$) methyl singlets at 72 and 60.

EXAMPLE 8

A mixture of 2.31 g. of cis-1,2,3,4,4a,5,10,10a-octahydro-5,5-dimethylbenzo[g]quinolin-7-ol, 1.0 g. of 35% aqueous formaldehyde solution, and 0.2 g. of 10% palladium-on-carbon catalyst was diluted to 100 ml. total volume with ethanol and shaken under 50 p.s.i. of hydrogen at room temperature. The theoretical quantity of hydrogen was consumed in three hours. The reaction mixture was filtered and the filtrate was evaporated under reduced pressure at room temperature. There was thus obtained 1.1 g. of cis-1,2,3,4,4a,5,10,-10a-octahydro-1,5,5,-trimethylbenzo[g]quinolin-7-ol as a white crystalline solid, m.p. 204°–207° C.; nmr (TFAA) showed methyl singlets at 86 and 78 Hz.

In similar fashion the trans compound was prepared in exactly the same manner as the corresponding cis compound. Thus, 2.0 g. of trans-1,2,3,4,4a,5,10,10a-octahydro-5,5-dimethylbenzo[g]quinolin-7-ol was catalytically hydrogenated to yield 1.4 g. of trans-1,2,3,4,4a,5,10,10a-octahydro-1,5,5-trimethylbenzo[g]-quinolin-7-ol as a white crystalline solid, m.p. 270°–272° C.; nmr (TFAA) showed methyl singlets at 86 and 72 Hz.

EXAMPLE 9

A mixture of 3.5 g. of cis-1,2,3,4,4a,5,10,10a-octahydro-5,5-dimethylbenzo[g]quinolin-7-ol, 1.7 g. of sodium bicarbonate, 40 ml. of dimethylformamide, and 219 g. of n-propyl iodide was stirred and refluxed for three hours and evaporated to dryness under reduced pressure. The residue was partitioned between water and diethyl ether. The ether layer was washed with water, dried, filtered, and treated with a slight excess of ethanolic hydrogen chloride. The supernatant liquid was decanted from the gum which precipitated, and the gum was dissolved in a small quantity of ethanol. Dilution with ether caused crystallization of 3.5 g. of solid, m.p. 263°–266° C. Recrystallization of this solid from ethanolether gave 3.15 g. of cis-1,2,3,4,4a,5,10,10a-octahydro-1-propyl-5,5-dimethylbenzo[g]quinolin-7-ol hydrochloride as an offwhite crystalline solid, m.p. 264°–266° C.; nmr (DMSO-$d_6$) methyl singlets at 74 and 70 Hz.

A mixture of 2.3 g. of trans-1,2,3,4,4a,5,10,10a-octahydro-5,5-dimethylbenzo[g]quinolin-7-ol, 0.8 g. of sodium bicarbonate, 30 ml. of dimethylformamide, and 1.7 g. (0.01 mole) of n-propyl iodide was stirred and refluxed for five hours and evaporated to dryness under reduced pressure. The residue was partitioned between water and chloroform. The chloroform layer was dried, filtered, and chromatographed on 110 g. of Grade III alumina, eluting with chloroform. The product fractions (as determined by thin layer chromatographic analysis) were combined, evaporated to dryness, taken up in ethanol, acidified with ethanolic hydrogen chloride, and diluted with diethyl ether to give 1.6 g. of solid, m.p. >290° C. This material was recrystallized from ethanol-ether to yield trans-1,2,3,4,4a,5,10,10a-octahydro-1-propyl-5,5-dimethylbenzo[g]quinolin-7-ol hydrochloride as an off-white crystalline solid, m.p. >300° C.; nmr (DMSO-$d_6$) showed methyl singlets at 76 and 63 Hz.

EXAMPLE 10

A mixture of 3.5 g. of cis-1,2,3,4,4a,5,10,10a-octahydro-5,5-dimethylbenzo[g]quinolin-7-ol, 2.0 g. of sodium bicarbonate, 40 ml. of dimethylformamide, and 1.7 g. of allyl bromide was stirred and refluxed for one and one-half hours. The reaction mixture was evaporated to dryness under reduced pressure, and the residue was partitioned between water and ether. The aqueous layer was extracted with diethyl ether, and the combined ether layers were washed with water, dried, and filtered. The filtrate was acidified with a slight excess of ethanolic hydrogen chloride and filtered to give 4.3 g. of solid, m.p. 262°–268° C. Recrystallization of this product from ethanol-ether yielded 3.3 g. of cis-1-allyl-1,2,3,4,4a,5,10,10a-octahydro-5,5-dimethylbenzo[g]quinolin-7-ol hydrochloride as a tan solid which melted at 271°–273° C.; nmr (DMSO-$d_6$) methyl singlets at 77 and 72 Hz.

A mixture of 2.3 g. of trans-1,2,3,4,4a,5,10,10a-octahydro-5,5-dimethylbenzo[g]quinolin-7-ol, 0.8 g. of sodium bicarbonate, 30 ml. of dimethylformamide, and 1.3 g. of allyl bromide was stirred and refluxed for one and one-half hours and then evaporated to dryness under reduced pressure. The residue was partitioned between water and chloroform. Spontaneous crystallization occurred in the chloroform layer. This product was collected on a filter. It weighed 2.2 g. and melted at 215°–222° C. By recrystallization of this solid from dimethylformamide, washing with ethanol, and drying at 50° C. in vacuo, there was obtained 2.15 g. of trans-1,2,3,4,4a,5,10,10a-octahydro-1-allyl-5,5-dimethylbenzo[g]quinolin-7-ol, as an off-white solid which melted at 215°–218° C.; nmr (TFAA) methyl singlets at 87 and 72 Hz.

EXAMPLE 11

A mixture of 3.46 g. of cis-1,2,3,4,4a,5,10,10a-octahydro-5,5-dimethylbenzo[g]quinolin-7-ol, 2.5 g. of 1-bromo-3-methyl-2-butene, 1.7 g. of sodium bicarbonate and 40 ml. of dimethylformamide was stirred and refluxed for three hours. The reaction mixture was filtered and methanol was used in a rinse. The filtrate, including the rinse liquid, was concentrated under reduced pressure and the resulting residual product was partitioned between chloroform and water. The chloroform layer was separated, washed with water, dried, treated with decolorizing charcoal, and filtered. The filtrate was concentrated under reduced pressure to yield 5.5 g. of dark red syrup. This syrup was dissolved in acetone and the solution was cooled. The crystalline solid was separated from solution was collected on a filter, washed with cold acetone, and dried at 76° C. There was thus obtained 3.5 g. of product which melted at 168°–172° C. By recrystallization of 2.0 g. of this product from acetone there was obtained 1.4 g. of cis-1,2,2,4,4a,5,10,10a-octahydro-1-(3-methyl-2-butenyl)-5,5-dimethylbenzo[g]quinolin-7-ol as an off-white crystalline solid, m.p. 170°–173° C.

EXAMPLE 12

A mixture of 1.5 g. of cis-1,2,3,4,4a,5,10,a-octahydro-1-(3-methyl-2-butenyl)-5,5-dimethylbenzo[g]quinolin-7-ol and 15 ml. of acetic anhydride was heated on a steam bath for forty-five minutes. The reaction mixture was concentrated under reduced pressure and the residue was dissolved in diethyl ether. The ether solution was washed with a cold, saturated aqueous sodium bicarbonate solution, dried, treated with decolorizing charcoal, and filtered. The filtrate was concentrated to yield 1.6 g. of a syrup. This product was dissolved in 15 ml. of ethyl acetate and acidified with ethereal hydrogen chloride. The crystalline solid which precipitated was collected on a filter, washed with diethyl ether, and dried at 70° C. This product, m.p. 246°–248° C. (dec.), which weighed 1.6 g. was recrystallized from ethanol-diethyl ether and dried at 70° C. There was thus obtained 1.1 g. of cis-1,2,3,4,4a,5,10,10a-octahydro-1-(3-methyl-2-butenyl)-5,5-dimethyl-7-acetoxybenzo[g]quinoline hydrochloride as a white crystalline solid, m.p. 251°–252° C. (dec.).

EXAMPLE 13

A solution of 3.5 g. of cis-1,2,3,4,4a,5,10,10a-octahydro-5,5-dimethylbenzo[g]quinolin-7-ol hydrobromide in 60 ml. of pyridine was stirred while 2.4 g. of cyclopropanecarbonyl chloride was added dropwise. Stirring was continued three hours after addition of the acid chloride was completed. The mixture was evaporated to dryness under reduced pressure and the residue was partitioned between water and diethyl ether. The ether layer was washed with dilute hydrochloric acid, saturated aqueous sodium bicarbonate solution, dried, filtered, and evaporated to dryness under reduced pressure. There was thus obtained 3.7 g. of cis-1,2,3,4,4a,5,10,10a-octahydro-1-cyclopropanecarbonyl-5,5-dimethyl-7-(cyclopropanecarbonyloxy)benzo[g]quinoline.

When 3.25 g. of trans-1,2,3,4,4a,-5,10,10a-octahydro-5,5-dimethylbenzo[g]quinolin-7-ol hydrobromide was used in the above procedure instead of the cis isomer, there was obtained as the product 3.06 g. of trans-1,2,3,4,4a,5,10,10a-octahydro-1-cyclopropanecarbonyl-5,5,-dimethyl-7-(cyclopropanecarbonyloxy)-benzo[g]quinoline.

EXAMPLE 14

A solution of 3.7 g. of cis-1,2,3,4,4a,5,10,10a-octahydro-1-cyclopropanecarbonyl-5,5-dimethyl-7-(cyclopropanecarbonyloxy)benzo[g]quinoline in 40 ml. of tetrahydrofuran was added dropwise to an ice-cold, stirred suspension of 0.8 g. of lithium aluminum hydride in 10 ml. of tetrahydrofuran. After this addition was completed, the mixture was refluxed for 8 hours. After cooling the reaction mixture, 1.6 ml. of water was added dropwise and the mixture was then diluted with tetrahydrofuran and filtered through Filter-Cel. The residue was washed with hot tetrahydrofuran and the filtrate and wash were combined and evaporated to dryness under reduced pressure to give 3.0 g. of crude product. This material was taken up in diethyl ether and treated with a slight excess of ethanolic hydrogen chloride. The hydrochloride which precipitated was recrystallized from ethanol-ether to yield 1.1 g. of cis-1,2,3,4,4a,5,10,10a-octahydro-1-cyclopropylmethyl-5,5-dimethylbenzo[g]quinolin-7-ol hydrochloride as a white crystalline solid, m.p. 267°–269° C; nmr (TFAA) showed methyl singlets at 87 and 80 Hz.

Using 3.06 g. of trans-1,2,3,4,4a,5,10,10a-octahydro-1-cyclopropanecarbonyl-5,5-dimethyl-7-(cyclopropanecarbonyloxy)-benzo[g]quinoline as the starting material in the reduction procedure above instead of the corresponding cis isomer, there was obtained as the product 1.6 g. of trans-1,2,3,4,4a,5,10,10a-octahydro-1-cyclopropylmethyl-5,5-dimethylbenzo[g]quinolin-7-ol hydrochloride as a white crystalline solid, m.p. 266° C. (dec.); nmr (TFAA) showed methyl singlets at 87 and 73 Hz.

EXAMPLE 15

To a stirred mixture of 3.12 g.. of cis-1,2,3,4,4a,5,10,10a-octahydro-5,5-dimethylbenzo[g]quinolin-7-ol and 60 ml. of pyridine cooled in an ice bath there was added dropwise a solution of 1.18 g. of dimethylcarbamyl chloride in 5 ml. of diethyl ether. Stirring and ice cooling were continued for ten minutes after this addition was completed, and then stirring without cooling was continued for three hours more. The crystalline precipitate which had separated was collected on a filter and washed with pyridine. The filtrate, including the wash liquid, was concentrated under reduced pressure and the residue thus obtained was partitioned between water and chloroform. The chloroform solution was washed with dilute hydrochloric acid, water, and saturated aqueous sodium bicarbonate solution and then dried, filtered, and concentrated under reduced pressure to yield 2.0 g. of a glassy residue. This residue was recrystallized first from acetone and then from ethanol thus yielding 0.8 g. of cis-1,2,3,4,4a,5,10,-10a-octahydro-1-dimethylcarbamyl-5,5-dimethylbenzo[g]quinolin-7-ol as a white crystalline solid which melted at 208°–210° C.

EXAMPLE 16

A. Proceeding in a manner similar to that described above in part F of Example 1, 41.2 g. of cis ethyl 1-benzyloxycarbonyl-2-(p-methoxybenzyl)-3-(p-piperidinecarboxylate was interacted in a Grignard reaction with ethylmagnesium bromide (prepared from 12.2 g. of magnesium turnings and 54.5 g. of ethyl bromide) to yield 41.8 g. of cis-1-benzyloxycarbonyl-2-(p-methoxybenzyl)-α,α-diethyl-3-piperidinemethanol.

B. Proceeding in a manner similar to that described above in part G of Example 1, 17.5 g. of cis-1-benzyloxycarbonyl-2-(p-methoxybenzyl)-α,α-diethyl-3-piperidinemethanol was converted to the hydrochloride and catalytically hydrogenated in the presence of palladium-on-charcoal catalyst to yield 10.7 g. of cis-2-(p-methoxybenzyl)-α,α-diethyl-3-piperidinemethanol.

C. Proceeding in a manner similar to that described above in part H of Example 1, 10.7 g. of cis-2-(p-methoxybenzyl)-α,α-diethyl-3-piperidinemethanol was heated with a mixture of 55 ml. of glacial acetic acid and 11 ml. of concentrated sulfuric acid to yield 9.0 g. of a mixture of the cis and trans forms of 1,2,3,4,4a,5,10,10a-octahydro-7-methoxy-5,5-diethylbenzo[g]quinoline as a syrup. By chromatographing this product on alumina, using a mixture of chloroform and methanol in a volume/volume ratio of 96/4, there was obtained 1.3 g. of cis-1,2,3,4,4a,5,10,10a-octahydro-7-methoxy-5,5-diethylbenzo[g]quinoline as a syrup. This base was converted to the hydrochloride, a white crystalline solid which melted at 193°–195° C.

EXAMPLE 17

Proceeding in a manner similar to that described above in Example 7, 3.0 g. of cis-1,2,3,4,4a,5,10,10a-octahydro-7-methoxy-5,5-diethylbenzo[g]quinoline hydrochloride was heated with 30 ml. of 48% hydrobromic acid to yield 2.4 g. of cis-1,2,3,4,4a,5,10,10a-octahydro-5,5-diethylbenzo[g]quinolin-7-ol hydrobromide as a white crystalline solid.

EXAMPLE 18

Proceeding in a manner similar to that described above in Example 10, 2.37 g. of cis-1,2,3,4,4a,5,10,10a-octahydro-5,5-diethylbenzo[g]quinolin-7-ol hydrobromide, 0.92 g. of allyl bromide, and 1.2 g. of sodium bicarbonate were interacted in 24 ml. of dimethylformamide to yield 1.3 g. of cis-1,2,3,4,4a,5,10,10a-octahydro-1-allyl-5,5-diethylbenzo[g]quinolin-7-ol as a white crystalline solid, m.p. 130°–133° C. When recrystallized from acetone this compound melted at 132°–134° C.

EXAMPLE 19

A. A mixture of 9.8 g. of magnesium turnings, 12 g. of bromobenzene, and an iodine crystal in 28 ml. of anhydrous diethyl ether was stirred until there was evidence that the reaction had started. Then 280 ml. of anhydrous diethyl ether was added, and 50.8 g. of bromobenzene was dripped in at a rate sufficient to maintain refluxing. After this addition was completed, the reaction mixture was refluxed for thirty minutes. There was then added, with stirring, 12.0 g. of cis ethyl 1-benzyloxycarbonyl-2-(p-methoxybenzyl)-3-piperidinecarboxylate in 400 ml. of anhydrous diethyl ether. The resulting reaction mixture was refluxed for five hours and then quenched with dilute hydrochloric acid. The ether layer was separated, washed with 1N sodium hydroxide solution and with water, and filtered over anhydrous calcium sulfate. The filtrate was concentrated under reduced pressure to yield 50 g. of cis-1-benzyloxycarbonyl-2-(p-methoxybenzyl)-α,α-diphenyl-3-piperidinemethanol as a crystalline residue. When a sample of this compound was recrystallized from ethanol there was obtained the ethanolate, $C_{14}H_{35}NO_4 \cdot C_2H_5OH$, as a white crystalline solid which melted at 90°–110° C. (dec.).

B. A mixture of 50 g. of cis-1-benzyloxycarbonyl-2-(p-methoxybenzyl)-α,α-diphenyl-3-piperidinemethanol, 250 ml. of glacial acetic acid, and 50 ml. of concentrated sulfuric acid was heated on a steam bath for ten minutes and then was poured over ice. The mixture was made basic by addition of a 35 percent aqueous solution of sodium hydroxide and extracted with diethyl ether. The ether extract was washed twice with water, dried, treated with decolorizing charcoal, and filtered. The filtrate was concentrated to yield 40 g. of a syrup. This product was taken up in 80 ml. of ethanol and concentrated under reduced pressure. The resulting residue crystallized slowly. The crystalline solid was mixed with 40 ml. of ethanol, the mixture was filtered, and the solid thus collected was washed with ethanol, the filtrate, including the wash liquor, being retained. This first crop of crude product weighed 2.1 g. The retained filtrate and wash liquor were combined and concentrated under reduced pressure. The residue thus obtained was partitioned between diethyl ether and dilute phosphoric acid. The aqueous layer was separated, washed with diethyl ether, and made basic with ammonium hydroxide. The oil which formed was extracted with diethyl ether and the ether extract was washed with water, dried, treated with decolorizing charcoal, and filtered. The filtrate was concentrated to yield 26 g. of a syrup. By chromatographing on alumina using benzene and chloroform, there was obtained from 10 g. of this syrup a second crop of crude product which weighed 3.2 g. This was combined with the first crop and recrystallized twice from ethanol to yield 3.0 g. of cis-1,2,3,4,4a,5,10,10a-octahydro-7-methoxy-5,5-diphenylbenzo[g]quinoline as a white crystalline solid which melted at 135°–137° C.

EXAMPLE 20

A. Using a procedure similar to that described above in part A of Example 1, 106 g. of diethyl (2-cyanoethyl)malonate was interacted with 21.9 g. of sodium hydride, and this product was interacted with 77.5 g. of phenylacetyl chloride to yield 152 g. of crude diethyl (phenylacetyl)(2-cyanoethyl)-malonate.

B. Using a procedure similar to that described above in part B of Example 1, 152 g. of crude diethyl (phenylacetyl)(2-cyanoethyl)malonate was catalytically reduced in the presence of platinum catalyst, and the reduction product treated was with hydrochloric acid to yield 104 g. of crude diethyl 2-benzyl-3,3-piperidinedicarboxylate hydrochloride as a white crystalline solid which melted at 182°–184° C. (dec.). When purified by recrystallization from ethanolic hydrogen chloride solution and from isopropyl alcohol, this compound melted at 188° C. (dec.).

By interaction of 38.6 g. of diethyl 2-benzyl-3,3-piperidinedicarboxylate with 19.1 g. of p-toluenesulfonyl chloride in the presence of 300 ml. of pyridine there was obtained 34.1 g. of diethyl 1-(p-toluenesulfonyl)-2-benzyl-3,3-piperidinedicarboxylate which melted at 116°–118° C. g.

By interaction of 40.4 g. of diethyl 2-benzyl-3,3-piperidinedicarboxylate with 13.4 g. of ethyl chloroformate in the presence of aqueous sodium hydroxide solution and chloroform there was obtained 35.5g. of crude triethyl 2-benzyl-1,3,3-piperidinetricarboxylate as a white crytalline solid which melted at 72°–76° C. A 5.0 g. portion was recrystallized from hexane to yield 4.0 g. of purified product which melted at 77°–80° C.

C. Proceeding in a manner similar to that described above in part C of Example 1, 104 g. of crude diethyl 2-benzyl3,3-piperidinedicarboxylate hydrochloride was interacted with 55.0 g. of benzyloxycarbonyl chloride to produce 130 g. of crude diethyl 1-benzyloxycarbonyl-2-benzyl-3,3-piperidinedicarboxylate as an orange-colored oil. The pure compound was a white crystalline solid, m.p. 66°–70° C. (dec.).

D. Using a procedure similar to that described in part D of Example 1, 130 g. of crude diethyl 1-benzyloxycarbonyl-2-benzyl-3,3-piperidinedicarboxylate was half-hydrolyzed with 18.8 g. of 86 percent potassium hydroxide to yield 76.6 g. of crude 1-benzyoxycarbonyl-2-benzyl-3-carbethoxy-3-piperidinecarboxylic acid as a white crystalline solid which melted at 169° C. (dec.). When purified by recrystallization from ethanol, this compound melted at 182°–184° C. (dec.).

E. Following a procedure similar to that described above in part E of Example 1, 75.6 g. of crude 1-benzyloxycarbonyl-2-benzyl-3-carbethoxy-3-piperidinecarboxylic acid was decarboxylated to yield 60.4 of crude ethyl 1-benzyloxycarbonyl-2-benzyl-3-piperidinecarboxylate.

F. Following a procedure similar to that described above in part F of Example 1, 60.4 g. of crude ethyl 1-benzyloxycarbonyl-2-benzyl-3-piperidinecarboxylate was interacted in a Gringnard reaction with methylmagnesium iodide (prepared from 11.5 g. of magnesium and 67.5 g. of methyl iodide) to yield 53.1 g. of crude 1-benzyloxycarbonyl-2-benzyl-$\alpha,\alpha$-dimethyl-3-piperidinemethanol.

G. Following a procedure similar to that described above in part G of Example 1, 53.1 g. of crude 1-benzyloxycarbonyl-2-benzyl-$\alpha,\alpha$-dimethyl-3-piperidinemethanol was converted to the hydrochloride and catalytically hydrogenated in the presence of palladium-on-charcoal catalyst to yield 20.3 g. of crude 2-benzyl-$\alpha,\alpha$-dimethyl-3-piperidinemethanol, m.p. 83°–104° C.

H. Hydrogen chloride was bubbled into a solution of 15.6 g. of 2-benzyl-$\alpha,\alpha$-dimethyl-3-piperidinemethanol in 75 ml. of nitrobenzene until the solution was acidic. The solution was cooled in an ice bath, and 15.6 g. of aluminum chloride was added in small portions. After this addition was completed, the temperature of the reaction mixture was allowed to rise to room temperature, and the mixture was stirred for three hours and then poured into water. A large volume of diethyl ether was added. The aqueous layer was separated and made strongly basic with 35 per cent sodium hydroxide solution and then extracted twice with diethyl ether. The ether extracts were combined and washed with water, dried, and filtered. The filtrate was evaporated under reduced pressure to yield as a residue 13.0 g. of a crude mixture of the cis and trans forms of 1,2,3,4,4a,5,10,-10a-octahydro-5,5-dimethylbenzo[g]quinoline hydrochloride in an approximate cis/trans ratio of 1.4/1. A 2.0 g. portion of this product was chromatographed on alumina, using a chloroform-methanol mixture in a volume ratio of 96 to 4, to yield 0.3 g. of cis-1,2,3,4,4a,5,10,10a-octahydro-5,5-dimethylbenzo[g]quinoline hydrochloride as a white crystalline solid, m.p. 265°–266° C. (dec.), 0.45 g. of the trans hydrochloride as a white crystalline solid, m.p. 286°–287° C. (dec.), and approximately 1.3 g. of a cis-rich mixture of the cis and trans hydrochlorides.

EXAMPLE 21

A. Using a procedure similar to that described above in Example 6, 6.99 g. of crude 2-benzyl-$\alpha,\alpha$-dimethyl-3-piperidinemethanol was interacted with 5.73 g. of p-toluenesulfonyl chloride in 70 ml. of pyridine at room temperature to yield 3.0 g. of 1-(p-toluenesulfonyl)-2-benzyl-$\alpha,\alpha$-dimethyl-3-piperidinemethanol which melted at 171°–172° C.

B. Using a procedure similar to that described above in Example 6, 46.9 g. of 1-(p-toluenesulfonyl)-2-benzyl-$\alpha,\alpha$-dimethyl-3-piperidinemethanol was heated with a mixture of 250 ml. of glacial acetic acid and 50 ml. of concentrated sulfuric acid to yield 30.3 g. of crude 1,2,3,4,4a,5,10,10a-octahydro-1-(p-toluenesulfonyl)-5,5-dimethylbenzo[g]quinoline which melted at 138°–140° C. By recrystallization of this product from ethanol there was obtained 27.1 g. of cis-1,2,3,4,4a,5,10,10a-octahydro-1-(p-toluenesulfonyl)-5,5-dimethylbenzo[g]quinoline as a white crystalline solid, m.p. 142°–144° C.

C. 28.0 g. of cis-1,2,3,4,4a,5,10,10a-octahydro-1-(p-toluenesulfonyl)-5,5-dimethylbenzo[g]quinoline was reduced with 28.0 g. of lithium aluminum hydride in 560 ml. of tetrahydrofuran to yield 13.0 g. of cis-1,2,3,4,4a,5,10,10a-octahydro-5,5-dimethylbenzo[g]quinoline hydrochloride, identical with that described above in part H of Example 20.

EXAMPLE 22

By interaction with a mixture of 10 ml. of formic acid and 10 ml. of 35% aqueous formaldehyde solution, 4.3 g. of cis-1,2,4,4a,5,10,10a-octahydro-5,5-dimethylbenzo[g]quinoline was N-methylated to yield 2.1 g. of cis-1,2,3,4,4a,5,10,10a-octahydro-1,5,5-trimethylbenzo[g]quinoline as a clear liquid which boiled at 75° C. at 0.05 mm. pressure.

EXAMPLE 23

By interacting 4.3 g. of cis-1,2,3,4,4a,5,10,10a-octahydro-5,5-dimethylbenzo[g]quinoline with 3.7 g. of n-propyl iodide in the presence of 1.9 g. of sodium bicarbonate and 40 ml. of dimethylformamide in a procedure similar to that described above in Example 9, there was obtained 3.7 g. of 1,2,3,4,4a,5,10,10a-octahydro-1-propyl-5,5-dimethylbenzo[g]quinoline as a straw-colored liquid which boiled at 90°–99° C. at 0.05 mm. pressure.

EXAMPLE 24

Using a procedure similar to that described above in Example 10, 2.5 g. of cis-1,2,3,4,4a,5,10,10a-octahydro-5,5-dimethylbenzo[g]quinoline hydrochloride was converted to the free base by treatment with ammonia, and the free base was interacted with 1.33 g. of allyl bromide in the presence of 0.92 g. of sodium bicarbonate and 10 ml. of dimethylformamide to yield 1.7 g. of 1,2,3,4,4a,5,10,10a-octahydro-1allyl-5,5-dimethylbenzo[g]quinoline as a colorless oil which boiled at 84° C. at 0.05 mm. pressure.

EXAMPLE 25

By interacting 4.3 g. of cis-1,2,3,4,4a,5,10,10a-octahydro-5,5-dimethylbenzo[g]quinoline with 2.3 g. of cyclopropanecarbonyl chloride in pyridine in a manner similar to that described above in Example 13, there was obtained 5.0 g. of cis-1,2,3,4,4a,5,10,10a-octahydro-1-cyclopropanecarbonyl-5,5-dimethylbenzo[g]quinoline. When this product was reduced with 1.5 g. of lithium aluminum hydride in 60 ml. of tetrahydrofuran in a manner similar to that described above in Example 14, there was obtained 2.5 g. of cis-1,2,3,4,4a,5,10,10a-octahydro-1-cyclopropylmethyl-5,5-dimethylbenzo[g]quinoline as a clear liquid which boiled at 105° C. at 0.06 mm. pressure; $n_D^{25} = 1.5492$.

EXAMPLE 26

A. To a solution of sodium ethoxide obtained by dissolving 0.7 g. of sodium in 110 ml. of ethanol there was added 144 g. of ethyl p-methoxy-benzoylacetate (obtained by mixing ethyl p-methoxybenzoate with sodium hydride and interacting the resulting mixture with ethyl acetate). The resulting mixture was stirred for ten minutes and then 34.2 g. of acrylonitrile was added, and the reaction mixture was allowed to stand overnight at room temperature. The reaction mixture was then concentrated under reduced pressure. The residue was taken up in diethyl ether, washed with dilute acetic acid and with water, dried, and filtered. The filtrate was concentrated to yield a clear yellow oil which was vacuum-distilled. The fraction distilling at 180°–198° C. at 0.2 mm. pressure weighed 144.6 g. and had $n_D^{25} = 1.5341$. This product was ethyl α-(p-methoxybenzoyl)-γ-cyanobutyrate.

B. 144 g.. of ethyl α-(p-methoxybenzoyl)-γ-cyanobutyrate was diluted to a volume of 1400 ml. with glacial acetic acid, platinum oxide catalyst was added and the mixture was catalytically hydrogenated for 8 hours. The catalyst was removed by filtration and the filtrate was concentrated under reduced pressure. The resulting residue was partitioned between diethyl ether and dilute hydrochloric acid (85 ml. of concentrated hydrochloric acid in 500 ml. of water). The aqueous layer was separated and made basic with ammonium hydroxide, adding ice to cool the solution, and extracted twice with diethyl ether. The ether extract was washed with water, dried, and filtered. The filtrate was concentrated to yield 108 g. of residue which crystallized. This solid was dissolved in boiling hexane and the solution was cooled. The solid which separated from solution was collected on a filter and washed with hexane. There was thus obtained 94.4 g. of ethyl 2-(p-methoxyphenyl)-3-piperidinecarboxylate as a white crystalline solid which melted at 65°–70°C. Purification of a one gram portion by recrystallization from acetone yielded 1 g. of this product which melted at 70°–72° C.

C. Proceeding in a manner similar to that described in part F of Example 1, 66.7 g. of ethyl 2-(p-methoxyphenyl)-3-piperidinecarboxylate was reacted in Grignard reaction with methylmagnesium iodide (obtained from 36.4 g. of magnesium turnings and 213 g. of methyl iodide) to yield 46.7 g. of 2-(p-methoxyphenyl)-α,α-dimethyl-3-piperidinemethanol hydrochloride as a crystalline solid which melted at 246°–248° C.

D. To a stirred solution of 46.7 g. of 2-(p-methoxyphenyl)-α,α-dimethyl-3-piperidinemethanol in 450 ml. of nitrobenzene there was added 50 g. of aluminum chloride in small portions. After this addition was completed, the reaction mixture was stirred for 6 hours and allowed to stand overnight. The reaction mixture was poured into ice water. The mixture was shaken thoroughly and then the nitrobenzene layer was removed. The aqueous layer was acidified by addition of concentrated hydrochloric acid and filtered. The filtrate contained some nitrobenzene, which was removed, and the aqueous layer was washed twice with diethyl ether and then made slightly basic by addition of ammonium hydroxide. The precipitate which formed was collected on a filter and washed thoroughly with diethyl ether. There was thus obtained 28.2 g. of crude 1,2,3,4,4a,9b-hexahydro-7-methoxy-5,5-dimethyl-5H-indeno[1,2,b]pyridine hydrochloride as a white crystalline solid which melted at 280°–283° C. Purification of a one gram portion by recrystallization from methanol-diethyl ether yielded 0.6 g. of this product which melted at 289°–292° C.

EXAMPLE 27

Using a procedure similar to that described above in Example 7, 27.4 g. of crude 1,2,3,4,4a,9b-hexahydro-7-methoxy-5,5-dimethyl-5H-indeno[1,2,b]pyridine hydrochloride was hydrolyzed by heating with 150 ml. of 48% hydrobromic acid to yield 24.5 g. of 1,2,3,4,4a,9b-hexahydro-5,5-dimethyl-5H-indeno[1,2,b]pyridin-7-ol hydrobromide which melted at 284°–287° C. (dec.). Treatment of 7.5 g. of this salt with ammonium hydroxide yielded 5.5 g. of the corresponding free base which melted at 228°–232° C.

EXAMPLE 28

To a stirred mixture of 6.5 g. of 1,2,3,4,4a,9b-hexahydro-5,5-dimethyl-5H-indeno[1,2,b]pyridin-7-ol and 100 ml. of pyridine there was added dropwise 6.8 g. of cyclopropanecarbonyl chloride and the reaction mixture was stirred for eight and one-half hours and then allowed to stand overnight at room temperature. The reaction mixture was filtered and the solid thus collected was washed twice with pyridine. The filtrate and wash liquor were combined and concentrated under reduced pressure, and the resulting residue was partitioned between water and diethyl ether. The ether layer was washed successively with dilute hydrochlorid acid, saturated aqueous sodium bicarbonate solution, and water, and then dried and filtered. The filtrate was concentrated under reduced pressure to yield 10.2 g. of crude 1,2,3,4,4a,9b-hexahydro-1-(cyclopropanecarbonyl)-7-(cyclopropanecarbonyloxy)-5,5-dimethyl-5H-indeno[1,2,b]pyridine When a 0.4 g. portion was recrystallized from hexane there was obtained 0.3 g. of this product which melted at 105°–109° C.

EXAMPLE 29

A solution of 9.8 g. of 1,2,3,4,4a,9b-hexahydro-1-cyclopropanecarbonyl-7-cyclopropanccarbonyloxy-5,5-dimethyl-5H-indeno[1,2,b]pyridine in 80 ml. of tetrahydrofuran was added dropwise to 2.1 g. of lithium aluminum hydride covered with 20 ml. of tetrahydrofuran cooled in ice. After this addition was completed, the reaction mixture was refluxed for six hours, allowed to stand overnight at room temperature, and then 4.2 ml. of water was added dropwise. The mixture was diluted with tetrahydrofuran to a volume of 800 ml.; diatomaceous silica filter aid was added, and the mixture was boiled and filtered. The residue thus collected was washed with hot tetrahydrofuran, and the filtrate and wash liquor were combined and concentrated under reduced pressure to yield 7.2 g. of a glassy residue. This residue was crystallized from acetone to yield 3.8 g. of trans-1,2,3,4,4a,9b-hexahydro-1-cyclopropylmethyl-5,5-dimethyl-5H-indeno1,2b]pyridin-7-ol as an off-white crystalline solid which melted at 188°–190° C.

EXAMPLE 30

A mixture of 5.0 g. of cis-1,2,3,4,4a,5,10,10a-octahydro-5,5-dimethylbenzo[g]quinoline hydrochloride, 3.7 g. of bromoacetaldehyde dimethyl acetal, 3.4 g. of sodium bicarbonate, and 50 ml. of dimethylformamide was stirred and refluxed for four and one-quarter hours. The reaction mixture was filtered and the filtrate was concentrated under reduced pressure. The resulting residue was partitioned between water and diethyl ether, and the ether layer was separated, washed twice with water, dried, and filtered. The filtrate was concentrated under reduced pressure to yield 5.3 g. of residue which was vacuum-distilled to yield 3.2 g. of cis-1,2,3,4,4a,5,10,10a-octahydro-5,5-dimethylbenzo[g]quinoline-1-acetaldehyde dimethyl acetal as a clear liquid, b.p. 125° C. at 0.08 mm.; $n_D^{25} = 1.5306$.

EXAMPLE 31

Proceeding in a manner similar to that described above in Example 30, 5.6 g. of trans-1,2,3,4,4a,5,10,-10a-octahydro-7-methoxy-5,5-dimethylbenzo[g]quinoline hydrochloride, 3.7 g. of bromoacetaldehyde dimethyl acetal, and 3.4 g. of sodium bicarbonate were interacted in 50 ml. of dimethylformamide to yield 5.0 g. of trans-1,2,3,4,4a,5,10,10a-octahydro-7-methoxy-5,5-dimethylbenzo[g]quinoline-1-acetaldehyde dimethyl acetal hydrochloride as a white crystalline solid which melted at 185° C. (dec.).

EXAMPLE 32

A. A solution of 11.6 g. of cis-1-benzyloxycarbonyl-2-(p-methoxybenzyl)-3-piperidinecarboxylic acid in 55 ml. of 30% hydrogen bromide in acetic acid was allowed to stand at room temperature for one-half hour, and then 55 ml. of diethyl ether was added and the precipitate which formed was filtered, washed with diethyl ether, and dried under reduced pressure over solid sodium hydroxide. There was thus obtained 9.0 g. of cis-2-(p-methoxybenzyl)-3-piperidinecarboxylic acid hydrobromide, m.p. 243°–245° C. (dec.).

B. A mixture of 9.9 g. of cis-2-(p-methoxybenzyl)-3-piperidinecarboxylic acid hydrobromide, 7.6 g. of sodium bicarbonate, 3.8 g. of benzyl chloride, and 100 ml. of dimethylformamide is stirred and refluxed for two hours. The reaction mixture is concentrated under reduced pressure, and the resulting residue is taken up in 100 ml. of water. By acidification with 30 ml. of N hydrochloric acid, there is produced cis-1-benzyl-2-(p-methoxybenzyl)-3-piperidinecarboxylic acid.

C. A solution of 33.9 g. of cis-1-benzyl-2-(P-methoxybenzyl)-3-piperidinecarboxylic acid in 340 ml. of diethyl ether is stirred at room temperature while 200 ml. of 1M methyl lithium is added dropwise. After this addition is completed, the reaction mixture is stirred and refluxed for four hours and poured over ice. The ether layer is separated and washed with 100 ml. of saturated aqueous sodium bicarbonate solution, dried, and filtered. The filtrate is concentrated to yield cis-3acetyl-1-benzyl-2-(p-methoxybenzyl)piperidine.

D. To the Grignard reagent prepared from 2.4 g. of magnesium turnings and 15.7 g. of bromobenzene in diethyl ether there is added dropwise an ethereal solution of 33.7 g. of cis-3-acetyl-1-benzyl-2-(p-methoxybenzyl)piperidine. After this addition is completed, the reaction mixture is stirred and refluxed for four hours and poured into aqueous ammonium chloride solution. The ether layer is separated, dried, and filtered. The filtrate is evaporated to dryness under reduced pressure to yield cis-1-benzyl-2-(p-methoxybenzyl)-α-methyl-α-phenyl-3-piperidinemethanol.

E. A solution of 41.5 g. of cis-1-benzyl-2-(p-methoxybenzyl)-α-methyl-α-phenyl-3-piperidinemethanol in 8.3 ml. of concentrated hydrochloric acid is diluted with dimethylformamide to a volume of 400 ml. and catalytically hydrogenated under 10 atmospheres of hydrogen in the presence of palladium-on-carbon catalyst. The catalyst is removed by filtration and the solvent is evaporated from the filtrate under reduced pressure. The resulting residue is taken up in ethanol and diluted with diethyl ether to yield cis-2-(p-methoxybenzyl)-α-methyl-α-phenyl-3-piperidinemethanol.

F. Using a procedure similar to that described above in part H of Example 1, cis-2-(p-methoxybenzyl)-α-methyl-α-phenyl-3-piperidinemethanol is cyclized to yield 1,2,3,4,4a,5,10,10a-octahydro-7-methoxy-5-methyl-5-phenylbenzo[g]quinoline. By N-alkylation of this compound with allyl bromide there is obtained 1,2,3,4,4a,5,10,10a-octahydro-7-methoxy-5-methyl-5-phenylbenzo[g]quinoline. Cleavage of this ether with concentrated hydrobromic acid yields 1,2,3,4,4a,5,10,-10a-octahydro-1-allyl-5-methyl-5-phenylbenzo[g]quinolin-7-ol.

EXAMPLE 33

Following the procedure described above in Example 10, but using 1,3-dichloro-1-propene instead of allyl bromide, there is obtained as the product 1,2,3,4,4a,5,10,10a-octahydro-1-(3-chloroallyl)-5,5-dimethylbenzo[g]quinolin-7-ol.

EXAMPLE 34

Follwing the procedure described above in Example 10, but using 3-cyanoallyl bromide instead of allyl bromide, there is obtained as the product 1,2,3,4,4a,5,10,-10a-octahydro-1-(3-cyanoallyl)-5,5-dimethylbenzo[g]quinolin-7-ol.

EXAMPLE 35

Following the procedure described above in Example 1, but starting with p-chlorophenylacetyl chloride instead of p-methoxyphenylacetyl chloride, there are obtained as the successive intermediate products in the reaction sequence: diethyl (p-chlorophenylacetyl) (2-cyanoethyl) malonate; diethyl 2-(p-chlorobenzyl)-3,3-piperidinedicarboxylate; 1-benzyloxycarbonyl-2-(p-chlorobenzyl)-3,3-piperidinedicarboxylate; 1-benzyloxycarbonyl-2-(p-chlorobenzyl)-3-carbethoxy-3-piperidinecarboxylic acid; ethyl 1-benzyloxycarbonyl-2-(p-chlorobenzyl)-3-piperidinecarboxylate; and 1-benzyloxycarbonyl-2-(p-chlorobenzyl)-α,α-dimethyl-3-piperidinemethanol, and as the cyclization product 1,2,3,4,4a,5,10,10a-octahydro-7-chloro-5,5-dimethylbenzo[g]quinoline. When this cyclization product is N-alkylated with n-propyliodiden there is obtained 1,2,3,4,4a,5,10,10a-octahydro-1-propyl-7-chloro-5,5-dimethylbenzo[g]quinoline.

EXAMPLE 36

A mixture of 2.6 g. of trans-enriched-1-benzyloxycarbonyl-2-(p-methoxybenzyl)-α,α-dimethyl-3-piperidinemethyanol, 13 ml. of glacial acetic acid, and 2.6 ml. of concentrated sulfuric aicd was heated on a steam bath for six minutes, poured into water, and extracted with diethyl ether. The aqueous layer was made basic with concentrated ammonium hydroxide and extracted with diethyl ether. The ether layer was washed with water, dried, and filtered, and the filtrate was evaporated to dryness under reduced pressure to give 0.8 g. of a mixture of the cis and trans forms of crude product. The nuclear magnetic resonance spectrum showed approximately 70 cis and 30% trans.

EXAMPLE 37

A mixture of 300 mg. of trans-2-(p-methoxybenzyl)-α,α-dimethyl-3-piperidinemethanol hydrochloride, 280 mg. of powdered potassium carbonate, 0.1 ml. of p-fluoronitrobenzene and 2.5 ml. of dimethyl sulfoxide was stirred and heated on a steam bath for one hour and poured into water and the mixture was extracted with diethyl ether. The ether extract was washed twice with water, dried, and filtered, and the filtrate was evaporated to dryness under reduced pressure to give 340 mg. of crude product. A thin layer chromatogram showed an intense yellow spot at $R_f = 0.36$ (chloroform with 2% of methanol). This product, which was trans-2-(p-methoxybenzyl)-α,α-dimethyl-1-(p-nitrophenyl)-3-piperidinemethanol, was isolated by preparative thin layer chromatography, and neither it nor its hydrochloride could be obtained crystalline; ir ($CHCl_3$) 3600 (OH), 1310 ($NO_2$), 1250 and 1030 (ether), and 820 $cm^{-1}$ (1,4-disubstituted benzene).

EXAMPLE 38

A. A mixture of 20 g. of neutral material recovered from the hydrogenolysis of cis-1-benzyloxycarbonyl-2-(p-methoxybenzyl)-α,α-dimethyl-3-piperidinemethanol and which had stood for several months, 2 g. of 10% palladium-on-carbon catalyst, and 200 ml. of ethanol was shaken under 50 p.s.i. of hydrogen until uptake ceased. The reaction mixture was filtered, and the collected solid was rinsed with ethanol. The filtrate and rinse were combined and evaporated to dryness under reduced pressure. The residue was partitioned between dilute hydrochloric acid and diethyl ether. The aqueous layer was washed with ether, made basic with concentrated ammonium hydroxide, and extracted with diethyl ether. The ether extract was dried and filtered. A thin layer chromatogram (silica, chloroform/3% isopropylamine) shows five compounds, $R_f$ 0.36 (cis carbinol, weak), 0.41 (trans carbinol, trace, 0.50 (strong), 0.53 (moderate), and 6.77 (trace). Treatment of the filtrate with a slight excess of etheral hydrogen chloride caused precipitation of a gummy mass. The supernatant liquid was decanted, and the gum was disolved in hot ethanol. Cooling for several hours at 0° C. gave 9.1 g. of 2-(p-methoxybenzyl)-3-isopropylidenepiperidine. This was twice recrystallized from ethanoldiethyl ether to give material which melted 255°–257° C. and gave a single spot on a thin layer chromatogram with $R_f$ 0.50, ir (KBr) 1660 (tetrasubstituted double bond) and 820 $cm^{-1}$ (1,4-disubstituted benzene); nmr ($CDCl_3$) 413 ($A_2B_2q,4$), 235 (t,1), J=7 cps, 223 (s,3), 196 (broad singlet, 3), 87 (d,3,J=1 cps), 200-50 (broad envelope, 9).

B. A mixture of 3.8 g. (0.013 moles) of 2-(p-methoxybenzyl)-3-isopropylidenepiperidine hydrochloride, 20 ml. of glacial acetic acid, and 4 ml. of concentrated sulfuric acid was heated on a steam bath for one hour, poured into water, made basic with concentrated ammonium hydroxide, and extracted with diethyl ether. The ether extract was washed with water, dried, and filtered, and the filtrate was evaporated to dryness under reduced pressure to give 3.4 g. (100%) of crude product. A thin layer chromatogram showed that cis-1,2,3,4,4a,5,10,10a-octahydro-7-methoxy-5,5-dimethylbenzo[g]quinoline was the major product and the corresponding trans isomer was a minor product. A nuclear magnetic resonance spectrum of this crude produce confirmed this and gave the cis: trans ratio as 80:20. Furthermore, a crystalline hydrochloride could be obtained which, after two recrystallizations from ethanol-diethyl ether, was identical in all respects ($R_f$, infrared spectrum, melting point and mixed melting point) with the cis product obtained by cyclization of the corresponding carbinol.

C. A mixture of 2.8 g. of 2-(p-methoxybenzyl)-3-isopropylidenepiperidine hydrochloride, 0.8 ml. of 35% aqueous formaldehyde solution, 1.4 ml. of triethylamine, and ethanol to a total volume of 50 ml. was shaken at room temperature under 50 p.s.i. of hydrogen. The theoretical quantity of hydrogen was consumed in one hour. The reaction mixture was filtered and the residue thus collected was rinsed with a small amount of ethanol. The filtrate and rinse were combined and evaporated to dryness under reduced pressure and the residue was partitioned between dilute ammonium hydroxide and diethyl ether. The ether layer was washed with water, dried, and filtered, and the filtrate evaporated to dryness under reduced pressure to give 1.9 g of 1-methyl-2-(p-methoxybenzyl)-3-isopropylidenepiperidine as a syrup. This was taken up in 50 ml. of diethyl ether and treated with a slight excess of ethereal hydrogen chloride to precipitate a gum. Addition of 5 ml. of isopropyl alcohol and trituration caused crystallization. Recrystallization from 5 ml. of isopropyl alcohol and 50 ml. of diethyl ether afforded the pure compound which melted at 179°–183° C; ir (KBr) 1670 $cm^{-1}$ (tetrasubstituted double bond); nmr (of base, $CDCl_3$): 147 (s,3); 93 (s,3); 63 (d3, J=1-2 cps).

D. A mixture of 1.0 g. of 2-(p-methoxybenzyl)-3-isopropylidenepiperidine hydrochloride, 1.1 g. of powdered potassium carbonate, 10 ml. of dimethyl sulfoxide, and 0.4 ml. of p-fluoronitrobenzene was stirred and heated on a steam bath for 1 hour. The reaction mixture was then poured into water and the water was decanted from the precipitated gum. The gum was washed with several portions of water and then taken up in diethyl ether, and the ether was washed with several portions of water. The ether was dried and filtered, and the filtrate was evaporated to dryness under reduced pressure to yield 1-(p-nitrophenyl)-2-(p-methoxybenzyl)-3-isopropylidenepiperidine as a residue. Neither the residue nor its hydrochloride could be induced to crystallize, although only one component could be observed on thin layer chromatographic analysis using several developing systems on both silica gel and alumina. The nuclear magnetic resonance spectrum ($CDCl_3$) of the crude residue showed: 439 ($A_2B_2$), 410, ($A_2B_2$), 295 (t,1,J=7 cps), 222 (a,3), 172 (d,2, J=7 cps), 95, (s,3), 76 (d,3,J=1-2 cps). The ultraviolet spectrum (95% ethanol) showed: 272S ($\epsilon$4100), 286S ($\epsilon$3500), 400 m ($\epsilon$16300); lit, p-methylanisole 277 ($\epsilon$2100), 284 ($\epsilon$1800); N,N-dimethyl-p-nitroaniline 395 ($\epsilon$20000).

E. A mixture of 1.9 g. of 2-(p-methoxybenzyl)-3-isopropylidenepiperidine hydrochloride, 1.7 g. of p-nitrobenzenesulfonyl chloride, 40 ml. of chloroform, and 2.4 ml. of triethylamine was allowed to stand in a closed vessel at room temperature for 24 hours. The reaction mixture was then washed with water, dilute hydrochloric acid, and saturated aqueous sodium bicarbonate solution, dried, and filtered, and the filtrate was evaporated to dryness under reduced pressure to give 3.5 g. of 1-(p-nitrobenzenesulfonyl)-2-(p-methoxybenzyl)-3-isopropylidenepiperidine as a syrup. This material was taken up in 35 ml. of hot ethanol and the solution allowed to cool. After filtration and washing the collected product with ethanol and drying under reduced pressure at 50° C., there was obtained 2.4 g. of the pure product which melted at 114°–116° C.; ir (KBr) 1670 (tetrasubstituted double bond), 1540 and 1350 ($NO_2$), and 1350 and 1150 ($SO_2$).

EXAMPLE 39

A. A mixture of 6.05 g. of cis-ethyl 1-benzyloxycarbonyl-3-piperidine carboxylate, 1 ml. of concentrated hydrochloric acid, and 100 mg. of 10% palladium-on-carbon catalyst was diluted to 60 ml. total volume with 95% ethyl alcohol and shaken under 4 atmospheres of hydrogen pressure at room temperature until one equivalent of hydrogen was consumed. After removal of the catalyst by filtration and evaporation of the filtrate, the basic fraction of the residue (dilute hydrochloric acid extraction follwed by liberation of the base with dilute ammonium hydroxide) was dried in diethyl ether over anhydrous calcium sulfate. The base hydrochloride crystallized twice from ethyl alcohol-diethyl ether to yield 3.0 g. of cis-ethyl 2-(p-methoxybenzyl)-3-piperidinecarboxylate hydrochloride, m.p. 139°–142° C.

By treatment with dilute ammonium hydroxide, 12.5 g. of cis-ethyl 2-(p-methoxybenzyl)-3-piperidinecarboxylate hydrochloride was converted to the free base, which was dried in diethyl ether solution, and the solution was then evaporated to dryness. The resulting residue was taken up in 100 ml. of tetrahydrofuran and the solution was added dropwise to an ice-cold suspension of 1.4 g. of lithium aluminum hydride in 100 ml. of tetrahydrofuran. Stirring was continued at room temperature for 3½ hours, 2.8 ml. of water was added, the mixture was filtered, and the solvent was evaporated from the filtrate. The residue thus obtained, 2-(p-methoxybenzyl)-3-piperidinemethanol, formed a crystalline p-toluenesulfonic acid salt. Two recrystallizations from ethyl alcohol yielded cis-2-(p-methoxybenzyl)-3-piperidinemethanol p-toluenesulfonate, a white solid, m.p. 175°–177° C.

In similar fashion, trans-2-(p-methoxybenzyl)-3-piperidinemethanol, a white solid, m.p. 113°–116° C. was prepared.

B. A solution of 10.4 g. of cis-2-(p-methoxybenzyl)-3-piperidinemethanol p-toluenesulfonate in 52 ml. of 48% hydrobromic acid was refluxed for 24 hours and the reaction mixture was then decanted hot from a small amount of tarry material. The decanted liquid crystallized on cooling. Filtration, washing with water, and recrystallization from ethyl alcohol yielded 2.0 g. of cis-1,2,3,4,4a,5,10,10a-octahydrobenzo[g]quinoline hydrobromide, m.p. 274°–278° C.

A suspension of 38 g. of this hydrobromide in 570 ml. of warm water was treated with 190 ml. of concentrated ammonium hydroxide, stirred on a steam bath for ½ hour, and cooled and filtered. The solid thus collected was washed with water, and the moist product was recrystallized from ethyl alcohol to yield 21.5 g. of cis-1,2,3,4,4a,5,10,10a-octahydrobenzo[g]quinolin-7-ol, an off-white solid, m.p. 233°–235° C. (dec.).

C. In analogous fashion, 4.5 g. of trans-2-(p-methoxybenzyl)-3-piperidinemethanol was refluxed with 39 ml. of 48% hydrobromic acid to yield trans-1,2,3,4,4a,5,10,10a-octahydrobenzo[g]quinolin-7-ol hydrobromide, m.p. 300°–360° C. with gradual decomposition. Treatment of this hydrobromide with ammonium hydroxide gave the free base as a white solid, m.p. 250°–252° C.

EXAMPLE 40

A. A mixture of 1.4 g. of cis-1,2,3,4,4a,5,10,10a-octahydrobenzo[g]quinolin-7-ol hydrobromide, 2.1 g. of sodium acetate trihydrate, and 14 ml. of acetic anhydride was stirred and heated on a steam bath for one hour. The solvent was evaporated from the mixture and the resulting residue was partitioned between water and diethyl ether. The ether layer was washed with saturated aqueous sodium bicarbonate solution, dried, and filtered, and the filtrate was evaporated. The residue thus obtained was crystallized from hexane to yield cis-1,2,3,4,4a,5,10,10a-octahydro-1-acetyl-7-acetoxybenzo[g]quinoline, m.p. 108°–1130° C. The nmr spectrum ($CDCl_3$) showed 3 aryl protons (400–430 Hz) and two methyl singlets (125, 133 Hz).

B. There was similarly prepared, from 2 g. of trans-1,2,3,4,4a,5,10,10a-octahydrobenzo[g]quinolin-7-ol hydrobromide, 3 g. of sodium acetate trihydrate, and 20 ml. acetic anhydride, trans-1,2,3,4,4a,5,10,10a-octahydro-1-acetyl-7-acetoxybenzo[g]quinoline, m.p. 124°–129° C. The nmr spectrum ($CDCl_3$) showed 3 aryl protons (400–430 Hz) and two methyl singlets (125, 133 Hz).

EXAMPLE 41

A. A mixture of 13.3 g. of cis-1,2,3,4,4a,5,10,10a-octahydrobenzo[g]quinolin-7-ol, 5.4 ml. of 35% aqueous formaldehyde solution, and 6 g. of palladium-on-carbon catalyst was diluted to 350 ml. total volume with ethyl alcohol and the mixture was shaken under 400 lbs./sq. in. of hydrogen until uptake ceased. Filtration to remove the catalyst, evaporation of the solvent and crystallization of the resulting residue from ethyl alcohol gave 10.8 g. of solid which on recrystallization from ethyl alcohol yielded cis-1,2,3,4,4a,5,10,10a-octahydro-1-methyl-benzo[g]quinolin-7-ol as a white solid, m.p. 213°–216° C.

B. In similar fashion, a mixture of 10.1 g. of trans-1,2,3,4,4a,5,10,10a-octahydrobenzo[g]quinolin-7-ol, 4.1 ml. of 35% aqueous formaldehyde solution, and 5 g. of palladium-on-carbon catalyst was hydrogenated to yield 7.1 g. of trans-1,2,3,4,4a,5,10,10a-octahydro-1-methylbenzo[g]quinolin-7-ol as an off-white solid, m.p. 240°–242° C.

EXAMPLE 42

A. A solution of 6.2 g. of cis-1,2,3,4,4a,5,10,10a-octahydro-1-methylbenzo[g]quinolin-7-ol in 250 ml. of ethyl alcohol was treated with an excess of ethereal diazomethane and allowed to stand for 24 hours. Evaporation of the solvent and distillation of the resulting residue gave 5.3 g. of cis-1,2,3,4,4a,5,10,10a-octahydro-1-methyl-7-methoxybenzo[g]quinoline as a clear liquid, b.p. 126° C./0.03 mm. Hg.

B. In similar fashion, there was prepared, from 3.6 g. of trans-1-methyl-1,2,3,4,4a,5,10,10a-octahydrobenzo[g]quinolin-7-ol in 150 ml. of ethyl alcohol, trans-1,2,3,4,4a,5,10,10a-octahydro-1-methyl-7-methoxybenzo[g]quinoline as a clear liquid, b.p. 112° C./0.05 mm. Hg.

EXAMPLE 43

A mixture of 7.0 g. of cis-1,2,3,4,4a,5,10,10a-octahydrobenzo[g]quinolin-7-ol, 2.9 g. of sodium bicarbonate, 4.6 g. of allyl bromide and 70 ml. of N,N-dimethylformamide was stirred and refluxed for 3 hours, and the reaction mixture was then evaporated to dryness. The resulting residue was partitioned between water and chloroform, the chloroform layer then being dried, charcoaled, and filtered, and the filtrate evaporated to remove the solvent. The residue thus obtained, which was cis-1,2,3,4,4a,5,10,10a-octahydro-1-allylbenzo[g]quinolin-7-ol, was dissolved in diethyl ether, the solution was filtered, and the filtrate was treated with a slight excess of ethanolic hydrogen chloride to give 7.3 g. of cis-1,2,3,4,4a,5,10,10a-octahydro-1-allylbenzo[g]quinolin-7-ol hydrochloride as a white solid. After recrystallization from methyl alcohol-diethyl ether, this product melted at 270°–272° C. (dec.) and weighed 5.2 g.

EXAMPLE 44

A mixture of 9.0 g. of cis-1,2,3,4,4a,5,10,10a-octahydrobenzo[g]quinolin-7-ol and 90 ml. of pyridine was stirred while 10.2 g. of cyclopropanecarbonyl chloride was added dropwise. Stirring was continued for three hours followed by removal of the solvent by evaporation. The resulting residue was partitioned between water and diethyl ether, the ether layer being washed first with N hydrochloric acid then with a saturated aqueous solution of sodium bicarbonate. Evaporation of the ether left a residue which was dissolved in 50 ml. of ethyl alcohol and 50 ml. of N sodium hydroxide solution. This solution was heated on a steam bath for 20 minutes, the ethyl alcohol was removed by evaporation, and the residual material was acidified with 50 ml. of N hydrochloric acid and extracted with diethyl ether. The ether extract was dried and the ether was removed by evaporation. The residue thus obtained was crystallized twice from ethyl alcohol to yield 2.3 g. of cis-1,2,3,4,4a,5,10,10a-octahydro-1-cyclopropanecarbonylbenzo[g]quinolin-7-ol as a white solid which melted at 179°–180° C.

EXAMPLE 45

A solution of 5.4 g. of cis-1-cyclopropanecarbonyl-1,2,3,4,4a,5,10,10a-octahydrobenzo[g]quinolin-7-ol in 60 ml. of warm tetrahydrofuran was added dropwise to a stirred suspension of 1 g. of lithium aluminum hydride in 30 ml. of tetrahydrofuran. After refluxing for 5 hours, the reaction mixture was quenched with 2 ml. of water and filtered. Evaporation of the filtrate left a solid residue which was recrystallized from acetone to yield 2.5 g. of cis-1,2,3,4,4a,5,10,10a-octahydro-1-cyclopropylmethylbenzo[g]quinolin-7-ol as a white solid, m.p. 176°–178° C.

EXAMPLE 46

A mixture of 7.1 g. of cis-1,2,3,4,4a,5,10,10a-octahydrobenzo[g]quinolin-7-ol hydrobromide, 4.2 g. of sodium bicarbonate, 4.3 n-propyl iodide, and 65 ml. of N,N-dimethylformamide was stirred and refluxed for 2½ hours, and the reaction mixture was then evaporated to dryness. The resulting residue was partitioned between water and chloroform and the chloroform layer was dried, charcoaled, and filtered, and the filtrate evaporated to remove the solvent. This residue thus obtained was crystallized three times from ethyl alcohol to yield 4.4 g. of cis-1,2,3,4,4a,5,10,10a-octahydro-1-propylbenzo[g]quinolin-7-ol as an off-white solid, m.p. 139°–142° C.

EXAMPLE 47

A. A suspension of 32.1 g. of cis-1-benzyloxycarbonyl-2-(p-methoxybenzyl)-3-piperidinecarboxylic acid in 670 ml. of anhydrous diethyl ether was cooled to 0° C., the air above the reaction surface was purged with nitrogen, and there was added in a fine stream 138 ml. of a 2.43M ethereal solution of methyl lithium. The reaction mixture was stirred for 4 hours at 0° C. and then poured into 1 liter of saturated aqueous ammonium chloride solution. The mixture was shaken and the ether layer was filtered and the filtrate was concentrated to yield 21.2 g. of residue which was crystallized from 55 ml. of ethyl alcohol. There was thus obtained 10.9 g. of cis-1-benzyloxycarbonyl-2-(p-methoxybenzyl)-3-acetylpiperidine as a white solid. After another recrystallization from ethyl alcohol, this compound melted at 84°–86° C.

B. A solution of 26.2 g. of cis-1-benzyloxycarbonyl-2-(p-methoxybenzyl)-3-acetylpiperidine in 525 ml. of diethyl ether was added in a fine stream to 2.6 g. of lithium aluminum hydride in 100 ml. of diethyl ether while stirring and cooling the reaction mixture in an ice-bath. After this addition was completed, the reaction mixture was stirred in an ice-bath for 4 hours and then poured into N hydrochloric acid. The ether layer was separated, washed with saturated aqueous sodium bicarbonate solution, dried, and filtered. The filtrate was concentrated to yield 24.6 g. of residue which was 1-benzyloxycarbonyl-2-(p-methoxybenzyl)-alpha-methyl-3-piperidinemethanol as a mixture of epimers. This product was dissolved in ethyl alcohol, 2.5 g. of palladium-on-carbon catalyst was added, and the mixture was then diluted to a total volume of 200 ml. with ethyl alcohol and catalytically hydrogenated. After 40 minutes, uptake of hydrogen ceased, the catalyst was removed by filtration, and the filtrate was concentrated. The resulting residue was partitioned between 100 ml. of N hydrochloric acid and 100 ml. of diethyl ether. The aqueous layer was made basic by addition of ammonium hydroxide, treated with potassium carbonate, and extracted twice with diethyl ether. The ether exracts were combined and evaporated to yield 13.9 g. of 2-(p-methoxybenzyl)-alpha-methyl-3-piperidinemethanol as a mixture of epimers.

B. 12.8 g. of 2-(p-methoxybenzyl)-alpha-methyl-3-piperidinemethanol, obtained as described above, in 130 ml. of 48% hydrobromic acid was refluxed for 24 hours, and the reaction mixture was then made basic by addition of concentrated ammonium hydroxide. The crystalline solid which formed was collected on a filter, washed with water, pressed dry, and slurried in methyl alcohol. The slurry was filtered and the solid thus collected, which weighed 7.7 g., was recrystallized from N,N-dimethylformamide and then heated in boiling methyl alcohol and filtered. The white solid thus collected, which weighed 4.2 g., was cis-5α-methyl-1,2,3,4,4a,5,10,10a-octahydrobenzo[g]quinolin-7-ol hemihydrobromide, m.p. >300° C.

EXAMPLE 48

A mixture of 4.2 g. of cis-5α-methyl-1,2,3,4,4a,5,10,10a-octahydrobenzo[g]quinolin-7-ol hemihydrobromide, 1.5 ml. of 35% aqueous formaldehyde solution, and 0.2 g. of palladium-on-carbon catalyst was diluted with ethyl alcohol to a volume of 100 ml. and catalytically hydrogenated for 2¼ hours to yield 2.0 g. of cis-1,2,3,4,4a,5,10,10a-octahydro-1,5α-dimethylbenzo[g]quinolin-7-ol as a white solid which melted at 203°–205° C.

EXAMPLE 49

A mixture of 5.2 g. of cis-1,2,3,4,4a,5,10,10a-octahydro-5α-methylbenzo[g]quinolin-7-ol hemihydrobromide, 2.5 g. of sodium bicarbonate, 3.4 g. of n-propyl iodide, and 50 ml. of N,N-dimethylformamide was stirred and refluxed for approximately 4 hours. The reaction mixture was worked up in a manner similar to that described above in Example 46 to yield 5.6 g. of cis-1,2,3,4,4a,5,10,10a-octahydro-1-propyl-5α-methylbenzo-[g]quinolin-7-ol, which was converted to 4.6 g. of the p-toluenesulfonate salt, a white solid, m.p. 214°–215° C.

EXAMPLE 50

A mixture of 5.2 g. of cis-1,2,3,4,4a,5,10,10a-octahydro-5α-methylbenzo[g]quinolin-7-ol hemihydrobromide, 2.5 g. of sodium bicarbonate, 2.4 g. of allyl bromide, and 50 ml. of N,N-dimethylformamide was stirred and refluxed for 2 hours. The reaction mixture was worked up in a manner similar to that described above in Example 43 to yeild 6.1 g. of crude cis-1,2,3,4,4a,5,10,10a-octahydro-1-allyl-5α-methylbenzo[g]quinolin-7-ol. This base was purified and a 2.5 g. portion of it was then converted to 3.5 g. of the p-toluenesulfonate salt, a white solid melting at 165°–170° C.

EXAMPLE 51

A mixture of 8.5 g. of cis-1,2,3,4,4a,5,10,10a-octahydro-5α-methylbenzo[g]quinolin-7-ol hemihydrobromide, 3.5 g. of sodium bicarbonate, 5.6 g. of cyclopropylmethyl bromide, and 80 ml. of N,N-dimethylformamide was stirred and refluxed for 2 hours. The reaction mixture was worked up to yield 9.1 g. of crude cis-1-cyclopropylmethyl-5α-methyl-1,2,3,4,4a,5,10,10a-octahydrobenzo[g]quinolin-7-ol. This base was purified and a 2.4 g. portion of it was then converted to 3.2 g. of the p-toluenesulfonate salt, a white solid melting at 199°–200° C. There was also prepared the methanesulfonate salt, an off-white solid which melted at 207°–210° C.

EXAMPLE 52

A mixture of 6.92 g. of cis-1,2,3,4,4a,5,10,10a-octahydro-5,5-dimethylbenzo[g]quinolin-7-ol, 2.52 g. of sodium bicarbonate, 2.98 g. of 2-methyl-2-propenyl chloride, and 60 ml. of N,N-dimethylformamide was stirred and refluxed for one hour. The reaction mixture was worked up in a manner similar to that described above in Example 11 to yield crude cis-1,2,3,4,4a,5,10,10a-octahydro-1-(2-methyl-2-propenyl)-5,5-dimethylbenzo[g]quinolin-7-ol. A 1.7 g. portion of the partially purified base was chromatographed on 170 g. of alumina (6% water) using diethyl ether as eluant, and the resulting syrupy product (1.3 g.) was recrystallized from hexane to yield 1.0 g. of the pure base as an off-white solid melting at 129°–131° C.

EXAMPLE 53

To a stirred solution of 6.92 g. of cis-1,2,3,4,4a,5,10,10a-octahydro-5,5-dimethylbenzo[g]quinolin-7-ol in 120 ml. of warm pyridine there was added dropwise 8.78 g. of cyclopentanecarbonyl chloride and the resulting reaction mixture was stirred for 5½ hours. The reaction mixture was worked up, using partitioning between water and diethyl ether, in a manner similar to that described in Example 13 to yield approximately 12 g. of crude cis-1,2,3,4,4a,5,10,10a-octahydro-1-cyclopentanecarbonyl-5,5-dimethyl-7-cyclopentanecarbonyloxybenzo[g]quinoline in which some solvent remained. This product in 75 ml. of tetrahydrofuran was added dropwise to 1.25 g. of lithium aluminum hydride in 25 ml. of tetrahydrofuran. After this addition was completed, the reaction mixture was stirred and refluxed for three hours. The reaction mixture was then worked up to yield crude cis-1,2,3,4,4a,5,10,10a-octahydro-1-(cyclopentylmethyl)-5,5-dimethylbenzo[g]quinolin-7-ol which was converted to the p-toluenesulfonate salt, an off-white solid melting at 220°–222° C.

EXAMPLE 54

A mixture of 6.92 g. of cis-1,2,3,4,4a,5,10,10a-octahydro-5,5-dimethylbenzo[g]quinolin-7-ol, 2.52 g. of sodium bicarbonate, 3.86 g. of cyclopenten-1-ylmethyl chloride, and 60 ml. of N,N-dimethylformamide was stirred and refluxed for forty-five minutes. The reaction mixture was concentrated under reduced pressure and the resulting residue was partitioned between 100 ml. of chloroform and 50 ml. of water. The chloroform layer was separated, washed with two 50 ml. portions of water, dried, charcoaled, and filtered. The filtrate was concentrated to yield 10.9 g. of residue which was taken up in 45 ml. of acetone, cooled and filtered to collect 7.2 g. of solid. This product was recrystallized from acetone and dried to yield 5.6 g. of cis-1,2,3,4,4a,5,10,10a-octahydro-1-(cyclopenten-1-ylmethyl)-5,5-dimethylbenzo[g]quinolin-7-ol as a white solid which melted at 179°–181° C.

EXAMPLE 55

A mixture of 5.0 g. of cis-1,2,3,4,4a,5,10,10a-octahydro-5,5-dimethylbenzo[g]quinoline, 1.9 ml. of ethyl chloroformate, 6.1 ml. of triethylamine, and 50 ml. of chloroform was allowed to stand overnight at room temperature. The mixture was washed in turn with 25 ml. portions each of water, dilute hydrochloric acid, and saturated aqueous sodium bicarbonate solution, dried, charcoaled and filtered. The filtrate was concentrated to yield 5.2 g. of residue from which there was obtained by distillation under reduced pressure 2.7 g. of cis-1,2,3,4,4a,5,10,10a-octahydro-1-carbethoxy-5,5-dimethylbenzo[g]quinoline as a straw-colored liquid, b.p. 135° C. at 0.02 mm. Hg.

EXAMPLE 56

A. To 134 g. of ethyl 2-phenyl-3-piperidinecarboxylate (obtained by catalytic hydrogenation of 191 g. of ethyl alpha-(2-cyanoethyl)benzoylacetate in glacial acetic acid in the presence of platinum oxide catalyst) in 400 ml. of chloroform there was added dropwise a solution of 68.6 g. of ethyl chloroformate in 200 ml. of chloroform. After half of this solution has been added, there was commenced dropwise simultaneous addition to the reaction mixture of a solution of 23.0 g. of sodium hydroxide in 460 ml. of water. After these additions were completed the mixture was stirred for about ten minutes, the chloroform layer was separated and washed successively with dilute hydrochloric acid, saturated aqueous sodium bicarbonate solution, and water. The chloroform solution was then dried and filtered, and the filtrate was concentrated to yield 172 g. of an orange-colored oil. This oil was distilled under reduced pressure. The fraction distilling at 140°–150° C. at 0.08–0.09 mm. Hg. weighed 150 g. This product was ethyl 1-carbethoxy-2-phenyl-3-piperidinecarboxylate; $n^{25} = 1.5128$.

To 30 g. of magnesium turnings in 80 ml. of diethyl ether there was added a crystal of iodine and, when the color had been discharged, 175 g. of methyl iodide in 160 ml. of diethyl ether was added dropwise at a rate sufficient to maintain refluxing. After this addition was completed, the reaction mixture was stirred for one-half hour, then was cooled in an ice bath and 115 g. of ethyl 1-carbethoxy-2-phenyl-3-piperidinecarboxylate in 140 ml. of diethyl ether was added dropwise. After this addition was completed, the ice bath was removed and the reaction mixture was stirred for 1 hour, then 200 ml. of diethyl ether was added and the mixture was refluxed for one and one-half hours. Water was added, the mixture was acidified by addition of hydrochloric acid, and a small amount of chloroform was added to dissolve a few crystals which appeared in the solution. The organic layer was washed with saturated aqueous sodium bicarbonate solution and with water, dried, and filtered. The filtrate was concentrated under reduced pressure to yield a crystalline residue. This residue was taken up in 110 ml. of boiling ethyl acetate, the solution was cooled in an ice bath, and the solid which separated from solution was collected on a filter, washed with ethyl acetate, and dried. There was thus obtained 64.6 g. of 1-carbethoxy-2-phenyl-α,α-dimethyl-3-piperidinemethanol, m.p. 118°–120° C. A second crop (3.5 g.) of this product, m.p. 115°–118° C., was recovered from the mother liquor.

To 13.2 g. of lithium aluminum hydride covered with 200 ml. of tetrahydrofuran and cooled in ice there was added dropwise 50.7 g. of 1-carbethoxy-2-phenyl-α,α-dimethyl-3-piperidinemethanol in 500 ml. of tetrahydrofuran. After this addition was completed, the reaction mixture was refluxed for 2½ hours and allowed to stand overnight. There was then added dropwise 26.4 ml. of water, the mixture was diluted with 500 ml. of tetrahydrofuran, diatomaceous silica filtering aid was added, and the mixture was boiled and filtered. The residue on the filter was extracted with one-half liter of boiling tetrahydrofuran and this extract was filtered and the residue on the filter was washed three times with boiling tetrahydrofuran. The combined filtrate was concentrated under reduced pressure to yield 40 g. of crystalline solid which was recrystallized from acetone to yield 29.0 g. of 2-phenyl-α,α-N-trimethyl-3-piperidinemethanol which was converted to its hydrochloride (32.0 g.), a white solid melting at 215°–217° C.

B. To a stirred mixture of 31.9 g. of 2-phenyl-α,α,N-trimethyl-3-piperidinemethanol hydrochloride and 120 ml. of carbon disulfide there was added in portions 31.9 g. of aluminum chloride. The reaction mixture, which refluxed spontaneously, was stirred for 2 hours and allowed to stand overnight. The carbon disulfide was removed by decantation, ice and water were added, and the mixture was made basic by addition of ammonium hydroxide and then was extracted with diethyl ether. The ether extract was dried and filtered and the filtrate was concentrated to yield 24.0 g. of a clear brown oil. By chromatogramming this oil on 1000 g. of silica and eluting with diethyl ether, there was obtained trans-1,2,3,4,4a,9b-hexahydro-1,5,5-trimethyl-5H-ideno[1,2-b]-pyridine which was converted to the hydrochloride, a white solid weighing 23.3 g. and melting at 214°–217° C. After recrystallization of a portion (7.4 g.) of this hydrochloride from ethyl alcohol-diethyl ether it melted at 215°–217° C. (weight 6.0 g.).

The following are further illustrative examples of the compounds of Formula I of this invention which are obtained in the manner taught hereinabove:

1,2,3,4,4a,5,10,10a-octahydro-1-cyclohexylmethyl-7-methanesulfonamido-5,5-dimethylbenzo[g]quinolin.

1,2,3,4,4a,5,10,10a-octahydro-1-propargyl-7-acetamido-5-methyl-5-phenylbenzo[g]quinoline.

1,2,3,4,4a,5,10,10a-octahydro-1-cyclopropyl-7-trifluoromethoxy-5,5-dimethylbenzo[g]quinoline.

1,2,3,4,4a,5,10,10a-octahydro-1-(cyclopenten-2-yl)-7-trifluoromethyl-5-methyl-5-ethylbenzo[g]quinoline.

1,2,3,4,4a,5,10,10a-octahydro-1-(3,3-dichloroallyl)-7-(3-pyridinecarbonyloxy)-5,5-diphenylbenzo[g]quinoline.

1,2,3,4,4a,9b-hexahydro-1-propyl-5,5-dimethyl-5H-indeno[1,2,b]pyridin-7-ol.

1,2,3,4,4a,9b-hexahydro-1-allyl-5,5-dimethyl-5H-indeno[1,2,b]pyridin-7-ol.

1,2,3,4,4a,9b-hexahydro-1-(3-chloroallyl)-5,5-diphenyl-5H-indeno[1,2,b]pyridin-7-ol.

1,2,3,4,4a,9b-hexahydro-1-(cyclopenten-3-yl)-7-ethanesulfonamido-5-methyl-5-ethyl-5H-indeno[1,2,b]pyridine.

1,2,3,4,4a,9b-hexahydro-1-(2-methyl-3-cyanoallyl)-7-trifluoromethoxy-5-propyl-5-phenyl-5H-indeno[1,2,b]pyridine.

1,2,3,4,4a,9b-hexahydro-1-(cyclobutyl)-7-bromo-5,5-dimethyl-5H-indeno[1,2,b]pyridine.

1,2,3,4,4a,5,10,10a-octahydro-1-(3-chloroallyl)-benzo[g]quinolin-7-ol.

1,2,3,4,4a,5,10,10a-octahydro-1-(3-chloroallyl)-5α-methylbenzo[g]quinolin-7-ol.

1,2,3,4,4a,5,10,10a-octahydro-1-cyclopropylmethyl-7-chlorobenzo[g]quinoline.

1,2,3,4,4a,5,10,10a-octahydro-1-(cyclobutylmethyl)-benzo[g]quinoline.

1,2,3,4,4a,5,10,10a-octahydro-1-(3-methyl-2-butenyl)-benzo[g]quinolin-7-ol.

1,2,3,4,4a,5,10,10a-octahydro-1-(3-chlorallyl)-5α-methylbenzo[g]quinoline.

1,2,3,4,4a,5,10,10a-octahydro-1-(3-chloroallyl)-7-(3,3-dimethylbutanoyloxy)-benzo[g]quinoline.

1,2,3,4,4a,9b-hexahydro-1-(3-methyl-2-butenyl)-5-methyl-7-acetoxy-5H[1,2,b]pyridine.

1,2,3,4,4a,9b-hexahydro-1-phenethyl-5H[1,2,b]pyridine.

1,2,3,4,4a,5,10,10a-octahydro-1-benzyl-7-nicotinoyloxybenzo[g]quinoline.

As indicated hereinabove, the 1,2,3,4,4a,5,10,10a-octahydro-1-($Y^1$)-7-($Y^2$)-5-($Y^3$)-5-($Y^4$)-benzo[g]quinolines and 1,2,3,4,4a,9b-hexahydro-1-($Y^1$)-7-($Y^2$)-5-($Y^3$)-5-($Y^4$)—5H—indeno[1,2,b]pyridines of this invention are useful as antagonists of strong analgesic agents such as meperidine and morphine. Generally speaking, the analgesic antagonist activity resides largely or entirely in cis form, the trans form ordinarily being either of low activity or inactive. Thus, when tested in rats by a modified D'Amour-Smith thermal stimulus test procedure, the compounds of Formula I were found to be antagonists of the analgesic activity of morphine and meperidine. In this test procedure, when the compounds of Formula I were administered prior to or simultaneously with administration or morphine or meperidine, the expected analgesic effect of the latter was decreased with increasing dosage levels of the former to a point where no analgesic effect was obtained. And when the new compounds were administered after the administration of morphine or meperidine, the analgesic effect was diminished or terminated, depending on the dosage levels involved. For example representative compounds of this invention, each in the form of an aqueous solution of the lactic acid acid-addition salt, were administered subcutaneously to rats to determine the dosage level, in terms of weight of antagonist per kilogram of body weight of the animal, which caused reduction of the analgesic effect of a 60 mg./kg. dose of meperidine hydrochloride by approximately 50 percent or 15 mg./kg. dose of morphine sulfate, so that the analgesic effect produced by the combination of the antagonist and the meperidine hydrochloride or the morphine sulfate was substantially the same as the analgesic effect produced by a 30 mg./kg. dose of meperidine hydrochloride alone or 7.5 mg./kg. of morphine sulfate alone, respectively. Representative test results thus obtained were as follows:

| Compound of Example No. | | mg./kg. versus meperidine | mg./kg. versus morphine |
| --- | --- | --- | --- |
| 8 | cis | 7.9 | |
|  | trans | inactive | |
| 9 | cis | 1.05 | 1.80 |
|  | trans | 14 | |
| 10 | cis | 0.46 | 1.05 |
|  | trans | 11 | |
| 11 | cis | 6.7 | |
|  | trans | 9.2 | |
| 14 | cis | 0.27 | 0.38 |
|  | trans | inactive | |
| 41A | cis | 1.1 | |
| 43 | cis | 0.16 | |
| 45 | cis | 0.16 | |
| 46 | cis | 0.11 | |

We claim:
1. 1-(Q)-2-[p-($Y^5$)-Phenyl-X-]-3-[($Y^3$)($Y^4$)methylidene]-piperidine, wherein X is —$CH_2$— or a valence bond; Q is hydrogen, alkyl having 1–6 carbon atoms, benzyl, p-nitrophenyl, acetyl, carbethoxy, benzyloxycarbonyl, p-toluenesulfonyl, or p-nitrobenzenesulfonyl; $Y^3$ and $Y^4$ are the same or different and are hydrogen, alkyl having 1–4 carbon atoms, or phenyl; and $Y^5$ is hydrogen, alkyl having 1–4 carbon atoms, halo, trifluoromethyl, or alkoxy having 1–4 carbon atoms.
2. A compound according to claim 1 wherein X is —$CH_2$—, Q is hydrogen, and $Y^5$ is methoxy.
3. A compound according to claim 2 wherein $Y^3$ and $Y^4$ are each methyl.

* * * * *